US009053353B2

(12) United States Patent
Timmis et al.

(10) Patent No.: US 9,053,353 B2
(45) Date of Patent: *Jun. 9, 2015

(54) IMAGE CLASSIFICATION OF GERMINATION POTENTIAL OF SOMATIC EMBRYOS

(75) Inventors: Roger Timmis, Olympia, WA (US); Mitchell R. Toland, Puyallup, WA (US); Timnit Ghermay, Ann Arbor, MI (US); William C. Carlson, Olympia, WA (US); James A. Grob, Auburn, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 1696 days.

This patent is subject to a terminal disclaimer.

(21) Appl. No.: 11/833,807

(22) Filed: Aug. 3, 2007

(65) Prior Publication Data
US 2007/0269096 A1    Nov. 22, 2007

Related U.S. Application Data

(60) Continuation of application No. 10/680,675, filed on Oct. 7, 2003, now abandoned, which is a division of application No. 09/700,037, filed as application No. PCT/US99/12128 on Jun. 1, 1999, now abandoned.

(60) Provisional application No. 60/087,524, filed on Jun. 1, 1998.

(51) Int. Cl.
| *G06K 9/00* | (2006.01) |
| *C12N 15/82* | (2006.01) |
| *A01C 1/00* | (2006.01) |
| *A01H 1/04* | (2006.01) |
| *A01H 4/00* | (2006.01) |

(52) U.S. Cl.
CPC ........ *G06K 9/00147* (2013.01); *C12N 15/8207* (2013.01); *A01C 1/00* (2013.01); *A01H 1/04* (2013.01); *A01H 4/00* (2013.01)

(58) Field of Classification Search
CPC ........... C12N 15/8207; C12N 15/8218; C12N 15/8249; C12N 15/873; C12N 9/0071; C12N 5/04
See application file for complete search history.

(56) References Cited

U.S. PATENT DOCUMENTS

| 5,181,259 A | 1/1993 | Rorvig |
| 5,183,757 A | 2/1993 | Roberts |
| 5,464,769 A | 11/1995 | Attree |
| 5,680,320 A | 10/1997 | Helmer |
| 5,784,162 A | 7/1998 | Cabib |
| 5,842,150 A | 11/1998 | Renberg |
| 5,930,803 A | 7/1999 | Becker |
| 5,960,435 A | 9/1999 | Rathmann |
| 6,021,220 A | 2/2000 | Anderholm |
| 6,092,059 A | 7/2000 | Straforini |
| 6,567,538 B1 | 5/2003 | Pelletier |
| 6,582,159 B2 | 6/2003 | McKinnis |
| 2002/0192686 A1 | 12/2002 | Adorjan |
| 2003/0055615 A1 | 3/2003 | Zhang |

OTHER PUBLICATIONS

Appeal Brief Under 37 CFR 41.37, filed Jan. 28, 2011, In re Patent Application of Mitchell R. Toland, U.S. Appl. No. 10/932,481, filed Sep. 2, 2004, Method for Classifying Plant Emryos Using Generalized Lorenz-Bayes Classifier.
Cheng, Z., and P.P. Ling, "Machine Vision Techniques for Somatic Coffee Embryo Morphological Feature Extraction," American Society of Agricultural Engineers 37(5):1663-1669, 1994.
Chi, C.-M., et al., "An Advanced Image Analysis System for Evaluation of Somatic Embryo Development," Biotechnology and Bioengineering 50(1):65-72, Apr. 1996.
Chi, C.-M., et al., "Spectral Approach to Population Dynamics of Carrot Somatic Embryos," Journal of Fermentation and Bioengineering 81(5):445-452, 1996.
Grob, J.A., et al., "Dimensional Model of Zygotic Douglas-Fir Embryo Development," Int'l Journal of Plant Sciences 160(4):653-662, 1999.
Timmis, R., "Bioprocessing for Tree Production in the Forest Industry: Conifer Somatic Embryogenesis," Biotechnology Progress 14(1):156-167, Feb. 1998.
Timmis, R., et al., "Use of Visible and Near Infrared Reflectance Spectra for Selection of Germination-Competent Somatic Embryos," Tree Biotechnology 2003, Abstract and Poster, Sweden, Jun. 2003.
Vits, H., et al., "Characterizing Patterns in Plant Somatic Embryo Cultures: Its Morphology and Development," AiChE Journal 40(10):1728-1740, 1994.

*Primary Examiner* — Blaine Lankford
(74) *Attorney, Agent, or Firm* — Baker Hostetler LLP

(57) ABSTRACT

The present invention is directed towards methods for the classification of plant embryos by the application of one or more classification algorithms to analyze digitized images and absorption, transmittance, or reflectance spectra. The methods are generally applicable and emphasize the importance of acquiring and using as much image and absorption, transmittance, or reflectance spectral information as possible, based on objective criteria. The present invention allows automated selection of embryos most suitable for further culture and rejection of those seen as less suitable.

18 Claims, 8 Drawing Sheets

IMAGE CLASSIFICATION OF GERMINATION POTENTIAL OF SOMATIC EMBRYOS

CROSS-REFERENCES TO RELATED APPLICATIONS

This is a continuation of U.S. patent application Ser. No. 10/680,675, filed Oct. 7, 2003, which is a divisional of U.S. patent application Ser. No. 09/700,037, filed Jul. 2, 2001, which is the National Stage of International Application No. PCT/US99/12128, filed Jun. 1, 1999, which in turn claims the benefit of U.S. Application No. 60/087,524, filed Jun. 1, 1998.

FIELD OF THE INVENTION

The present invention relates to classification of plant embryos for determination of suitability for germination or other treatments. In particular, it is concerned with selection of conifer somatic embryos most likely to be successfully germinated and to produce normal plants.

BACKGROUND

Reproduction of selected plant varieties by tissue culture has been a commercial success for many years. The technique has enabled mass production of genetically identical selected ornamental plants, agricultural plants and forest species. The woody plants in this last group have perhaps posed the greatest challenges. Some success with conifers was achieved in the 1970s using organogenesis techniques wherein a bud, or other organ, was placed on a culture medium where it was ultimately replicated many times. The newly generated buds were placed on a different medium that induced root development. From there, the buds having roots were planted in soil.

While conifer organogenesis was a breakthrough, costs were high due to the large amount of handling needed. There was also some concern about possible genetic modification. It was a decade later before somatic embryogenesis achieved a sufficient success rate so as to become the predominant approach to conifer tissue culture. With somatic embryogenesis, an explant, usually a seed or seed embryo, is placed on an initiation medium where it multiplies into a multitude of genetically identical immature embryos. These can be held in culture for long periods and multiplied to bulk up a particularly desirable clone. Ultimately, the immature embryos are placed on a development or maturation medium where they grow into somatic analogs of mature seed embryos. These embryos are then individually selected and placed on a germination medium for further development. Alternatively, the embryos may be used in manufactured seeds.

There is now a large body of general technical literature and a growing body of patent literature on embryogenesis of plants. Examples of procedures for conifer tissue culture are found in U.S. Pat. Nos. 5,036,007 and 5,236,841 to Gupta et al.; U.S. Pat. No. 5,183,757 to Roberts; U.S. Pat. No. 5,464,769 to Attree et al.; and U.S. Pat. No. 5,563,061 to Gupta.

One of the more labor intensive and subjective steps in the embryogenesis procedure is the selection from the maturation medium of individual embryos suitable for germination. The embryos may be present in a number of stages of maturity and development. Those that are most likely to successfully germinate into normal plants are preferentially selected using a number of visually evaluated screening criteria. Morphological features such as axial symmetry, cotyledon development, surface texture, color, and others are examined and applied as a pass/fail test before the embryos are passed on for germination. This is a skilled yet tedious job that is time consuming and expensive. Further, it poses a major production bottleneck when the ultimate desired output will be in the millions of plants.

It has been proposed to use some form of instrumental image analysis for embryo selection to replace the visual evaluation described above. For examples, refer to Cheng, Z. and P. P. Ling, "Machine Vision Techniques for Somatic Coffee Embryo Morphological Feature Extraction," Trans. Amer. Soc. Agri. Eng. 37:1663-1669 (1994), or Chi, C. M., C. Zhang, E. J. Staba, T. J. Cooke, and W-S. Hu, "An Advanced Image Analysis System for Evaluation of Somatic Embryo Development," Biotech. and Bioeng. 50:65-72 (1996). All of these methods require considerable pre-judgment of which morphological features are important and the development of mathematical methods to extract this information from the images. Relatively little of the information from the image has actually been used.

The problem of how to best use image analysis to automate the selection of somatic embryos after they had been separated from residual tissue, singulated, and imaged in color from multiple positions has not been successfully addressed. Various methods are known for extracting size and shape information from scanned images. As one example, Moghaddam et al., U.S. Pat. No. 5,710,833, describes a method useful for recognition of any multifeatured entity such as a human face. Sclaroff et al., U.S. Pat. No. 5,590,261, describes a method that can be used for object recognition purposes.

Where embryos are concerned, a further problem using scanning technology is that morphology differs between clones within a given species. The differences between acceptable and rejected embryos can be very subtle, varying by clone. Hence, the choice of selection criteria for machine use tends to be subjective, difficult to specify mathematically, and may be clone specific.

The development of high speed computers and new spectroscopic hardware has led to the development of new instruments which have the capability to rapidly acquire spectra on large numbers of samples. However, the acquisition of vast amounts of spectral data from a sample necessitates the development of similarly powerful data analysis tools to uncover subtle relationships between the collected spectra and the chemical properties of the sample. One such data analysis methodology, commonly known as chemometrics, applies multivariate statistical techniques to complex chemical systems in order to facilitate the discovery of the relationship between the absorption, transmittance or reflectance spectral data acquired from a sample and some specified property of the sample that is subject to independent measurement. The end result of multivariate analysis is the development of a predictive classification model that allows new samples of unknown properties to be rapidly and accurately classified according to a specified property based upon the acquired spectral data. For example, multivariate analysis techniques such as: principal component analysis (PCA) and a principal component-based method, projection to latent structures (PLS), have been used to explore the multivariate information in previous applications of near-infrared (NIR) spectroscopy to the pulp and paper industry to develop classification models for paper quality. See, for example, U.S. Pat. Nos. 5,638,284, 5,680,320, 5,680,321, and 5,842,150.

SUMMARY

The present invention is based on classification of plant embryos by the application of classification algorithms to digitized images and absorption, transmittance, or reflectance spectra of the embryos. The methods are generally applicable and emphasize the importance of acquiring and using as much image and absorption, transmittance, or reflectance spectral information as possible, based on objective criteria. One goal has been automated classification and selection of embryos most suitable for further culture and rejection of those seen as less suitable. The technique is capable of utilizing more complex imaging technology; e.g., multi-viewpoint images and images in color or from non-visible portions of the electromagnetic spectrum.

In one aspect of the present invention, a method for classifying plant embryos according to embryo quality is provided. The method first develops a classification model by acquiring raw digital image data of reference samples of plant embryos of known embryo quality. Optionally, the raw digital image data is preprocessed using one or more preprocessing algorithms to reduce the amount of raw image data yet retain substantially all of the image data that contains geometric and color information regarding the embryo or embryo organ. An example of such an optional preprocessing technique involves removing image data that is not derived from the plant embryo or plant embryo organ. Another optional preprocessing step results in the calculation of metrics which emphasize image features that are particularly important in embryo quality classification. Data analysis is performed on the raw digital image data, or on the preprocessed image data depending upon which method is followed, using one or more classification algorithms to develop a classification model for classifying plant embryos by embryo quality. During this data analysis one or more of the classification algorithms utilizes raw digital image data representative of more than just the embryo perimeter, or the preprocessed image data to develop the classification model. The embryo quality of the reference samples is determined by reference to such qualities as morphological comparison to normal zygotic plant embryos, determination of the reference embryo's conversion potential, resistance to pathogens, drought resistance and the like. Raw digital image data of plant embryos of unknown embryo quality is then acquired using the same methods as performed on the reference samples. The acquired raw digital image data is then analyzed using classification algorithms used to develop the classification model in order to classify the quality of the plant embryo of unknown quality. A more robust method is obtained by acquiring raw digital image data of multiple views of the embryo, such as end-on views of the embryo and/or longitudinal views.

In another aspect of the present invention plant quality is classified by developing a single metric classification model by acquiring raw digital image data of reference samples of whole plant embryos or any portion thereof from plant embryos of known embryo quality. A metric value is calculated from the acquired raw digital image data of each embryo of known quality. The metric values are divided into two sets of metric values based upon the known embryo quality. A Lorenz curve is calculated from each set of metric values. A threshold value is determined from a point on the Lorenz curve which serves as a single metric classification model to classify plant embryos by embryo quality. Raw image data is acquired from a whole plant embryo or any portion thereof from a plant embryo of unknown quality. The single metric classification model developed from embryos of know quality is applied to the raw image data acquired from plant embryos of unknown quality in order to classify the quality of the unknown plant embryo. Single metric classification models can optionally be combined using one or more classification algorithms to develop more robust classification models for classifying plant embryos by embryo quality.

In another embodiment of the present invention, plant embryo quality is classified by collecting absorption, transmittance or reflectance spectral raw data from plant embryos or portions thereof and processing the data using classification algorithms. The inventive method first requires that a classification model be developed by acquiring absorption, transmittance or reflectance spectral raw data of reference samples of plant embryos or portions thereof whose embryo quality is known. In one alternative embodiment, prior to making the classification model, the spectral raw data in whole or in specific parts is preprocessed to among other things, reduce noise and adjust for drift and diffuse light scatter. The classification model is then made by performing a data analysis using classification algorithms on the preprocessed spectral raw data. Absorption, transmittance or reflectance spectral raw data is then acquired from a plant embryo of unknown embryo quality. The spectral raw data collected from the embryo of unknown quality is either applied directly to the embryo quality classification model or preprocessed to reduce noise and adjust for drift and diffuse light scatter and then the preprocessed spectral data is applied to the classification model depending upon which method was used to make the classification model in use. In either case, the application of the unknown spectral data to the classification model allows classification of the quality of the plant embryo of unknown plant embryo quality.

DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION

Figure 1:
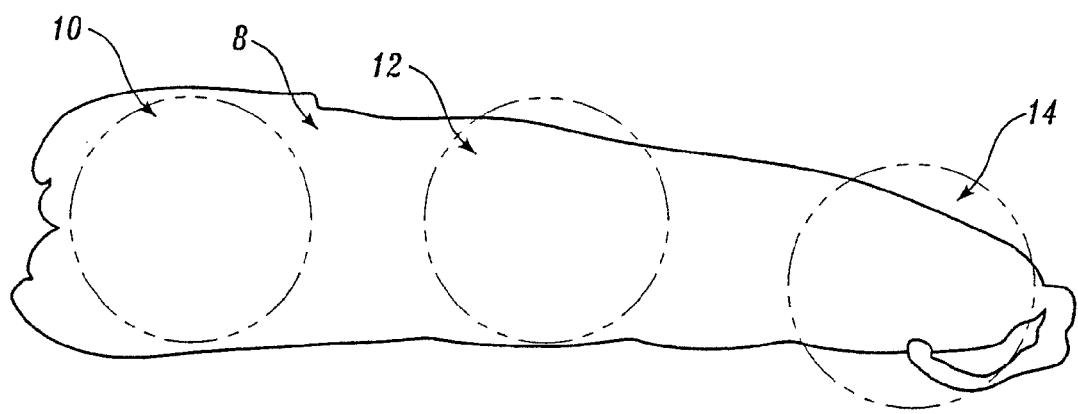
FIG. 1 shows a diagrammatic representation of a tree embryo 8. The circled areas represent the embryo regions representative of the three embryo organs known as cotyledon 10, hypocotyl 12, and radicle 14.

The inventive methods are used to classify any type of plant embryos, such as, for example, zygotic and somatic embryos, by any embryo quality that is amenable to characterization. For example, embryo quality can be defined using morphological criteria such as axial symmetry, cotyledon development, surface texture and color. As used herein "zygotic morphology" refers to morphological criteria, such as axial symmetry, cotyledon development, surface texture and color that are characteristic of a normal zygotic plant embryo. Alternatively, embryos can be classified using developmental or functional criteria, such as embryo germination and subsequent plant growth and development, often collectively referred to in the literature as "conversion." As used herein "conversion potential" refers to the capacity of a somatic embryo to germinate and/or survive and grow in soil, preceded or not by desiccation or cold treatment of the embryo. In addition, "plant embryo quality" refers to other plant characteristics such as resistance to pathogens, drought resistance, heat and cold resistance, salt tolerance, preference for light quality, suitability for long term storage of somatic embryos or any other plant quality susceptible to quantification.

Embryos from all plant species can be adapted to the inventive methods. The methods have particular application to agricultural plant species where large numbers of somatic embryos are used to propagate desirable genotypes such as with forest tree species. In particular, the methods can be used to classify somatic embryos from conifer tree family Pinaceae, particularly from the genera: *Pseudotsuga* and *Pinus*. A diagrammatic drawing of a *Pseudotsuga* tree embryo 8 is presented in FIG. 1 in which the general locations of the three embryo organs, cotyledon 10, hypocotyl 12, and radicle 14 are indicated.

In one embodiment of the present invention images of plant embryos or plant embryo organs are acquired in a digital form by scanning one or more views of the embryos or organs from multiple positions using known technology, such as electronic camera containing a charge couple devise (CCD) linked to a digital storage devise. A classification model for plant embryo quality is then developed by performing a data analysis on the digital image data using one or more classification algorithms. Examples of such classification algorithms include, but are not limited to, principal components analysis (see, for example, Jackson, J. E., *A User's Guide to Principal Components*, John Wiley and Sons, New York (1991); Jolliffe, I. T., *Principal Components Analysis*, Springer-Verlag, New York (1986); Wold, S., "Pattern Recognition by Means of Disjoint Principal Components Models," *Pattern Recognition* 8:127-139 (1976); and Watanapongse, P. and H. H. Szu, "Application of Principal Wavelet Component in Pattern Classification," *Proceedings of SPIE, Wavelet Applications V*, H. H. Szu, Editor, vol. 3391, pp. 194-205 (1998)), Artificial Neural Networks (Mitchell, Tom M., *Machine Learning*, WCB/McGraw-Hill pp. 112-115, (1997)), Bayesian Classifiers (Mitchell at 174-176), Probably Approximately Correct (PAC) Learning (Mitchell at 203-220), Radial Basis Functions which includes the statistical technique of fitting mixture distribution models to data (Mitchell, pp. 238-240), and Nearest-Neighbor Methods (Mitchell at 231-236). In addition to the aforementioned classification algorithms, a new classification algorithm is provided in the present invention to classify plant embryos based upon the Lorenz curve. For a brief introduction to Lorenz curves, see Johnson, S. and N. L. Kotz, Eds. *Encyclopedia of Statistical Sciences*, John Wiley, vol. 5, pp. 156-161 (1985).

It is also well known in the art of data analysis that several different algorithms besides Principal Component Analysis (PCA) can be used to develop and use classification models. More specifically, the following statistical techniques can also be adapted to the present invention: Partial Least Squares Regression, Principal Components Regression (PCR), Multiple Linear Regression Analysis (MLR), Discriminant Analysis, Canonical Correlation Analysis, Multivariate Multiple Regression, Classification Analysis, Regression Tree Analysis which includes Classification Analysis by Regression Trees (CART™, Salford Systems, San Diego, Calif.), and Logistic and Probit Regression. See U.S. Pat. No. 5,842, 150 and (Mitchell, Tom M., *Machine Learning*, WCB/McGraw-Hill pp. 112-115, 238-240 (1997)).

The classification model is deduced from a "training" data set of multiple images of plant embryos or plant embryo organs acquired from embryos having known embryo quality. Embryos providing the training set images are classified as acceptable or unacceptable based on biological fact data such as morphological similarity to normal zygotic embryos or proven ability to germinate or convert to plants. The inventive methods are generally adaptable to any plant quality that is susceptible to quantification. Unclassified embryos are classified as acceptable or not based on how close images of the unclassified embryos fit to the classification model developed from the training set groups.

As used herein the term "classification algorithm" refers to any sequence of mathematical or statistical calculations, formulae, functions, models or transforms of image or spectral data from embryos used for the purpose of classifying embryos according to embryo quality. A classification algorithm can have just one step or many. In addition, classification algorithms of the present invention can be constructed by combining intermediate classification models or single metric classification models through the use of mathematical algorithms such as the Bayes optimal classifier, neural networks or the Lorenz curve. Except for the single metric classification models, the image classification models of the present invention are derived from a data analysis of more than just embryo perimeter image data acquired from plant embryos or embryo organs during the training sessions that lead to the identification of an embryo quality classification model. That is, the classification models of the present invention, except for the single metric classification models, are developed using at least one classification algorithm which considers more of the acquired raw digital image data than required to define the perimeter of the embryo. Thus, the classification algorithms perform a data analyses that results in the development of a classification model from the image or spectral data without any subjective assumptions being made regarding which data features are important for embryo quality classification.

As used herein "embryo perimeter" means the pixels in raw digital image data or preprocessed digital image data which define the outer perimeter of an imaged embryo.

Optionally, the raw digital image data can be preprocessed using preprocessing algorithms. As used hereafter the term "preprocessing algorithm" refers to any sequence of mathematical or statistical calculations, formulae, functions, models or transforms of image or spectral data from embryos used for the purpose of manipulating image or spectral data in order to: 1) remove image or spectral data that is derived from non-embryo sources, i.e., background light scatter or other noise sources; 2) reduce the size of the digital data file that is used to represent the acquired image or spectra of the embryo while retaining substantially all of the data that represents informational features such as geometric embryo shape and surface texture, color, and light absorption, transmittance or reflectance, of the acquired image or spectra; and 3) calculate metrics from the acquired raw image or spectral data and from values obtained during other preprocessing steps, in order to identify and emphasize embryo data that is useful in development of an embryo quality classification model.

For example, U.S. Pat. No. 5,842,150 discloses that NIR spectral data can be preprocessed prior to multivariate analysis using the Kubelka-Munk transformation, the Multiplicative Scatter Correction (MSC), e.g., up to the fourth order derivatives, the Fourier transformation or by using the Standard Normal Variate transformation, all of which can be used to reduce noise and adjust for drift and diffuse light scatter.

Alternatively, the amount of digital data required to represent an acquired image or spectrum of an embryo can be reduced using preprocessing algorithms such as wavelet decomposition. See, for example, Chui, C. K., *An Introduction to Wavelets*, Academic Press, San Diego (1992); Kaiser, Gerald, *A Friendly Guide to Wavelets*, Birkhauser, Boston; and Strang, G. and T. Nguyen, *Wavelets and Filter Banks* Wellesley-Cambridge Press, Wellesley, Mass. Wavelet decomposition has been used extensively for reducing the amount of data in an image and for extracting and describing features from biological data. For example, wavelet techniques have been used to reduce the size of fingerprint image files to minimize computer storage requirements. A biological example is the development of a method for diagnosing obstructive sleep apnea from the wavelet decomposition of heart beat data. Wavelets enable rearrangement of the information in a picture of an embryo into size and feature categories. For example, size and shape data may be separated from texture. The results of a wavelet decomposition or functions thereof are then used as inputs to the classification algorithms described above. A variety of other interpolation methods can be used to similarly reduce the amount of data in an image or spectral data file, such as, calculation of adjacent averages, Spline methods (see, for example, C. de Boor, *A Practical Guide to Splines*, Springer-Verlag, (1978)), Kriging methods (see, for example, Noel A. C. Cressie, *Statistics for Spatial Data*, John Wiley, 1993)) and other interpolation methods which are commonly available in software packages that handle images and matrices.

Other preprocessing algorithms can be used to process data collected from an embryo in order to obtain the most robust correlation of the acquired data to embryo quality. For example, in Example 1 several statistical values were calculated to recapture some of the data information that was lost when a wavelet decomposition was used to reduce the size of the image. The recaptured information represented in the metrics allowed the development of a classification model that was better at predicting embryo quality than a model developed from principal component analysis of image data that was preprocessed using wavelet methods. As used hereinafter "metrics" refers to any scalar statistical value that captures geometric, color, or spectral features which contains information about the embryos, such as central and non-central moments, function of the spectral energy at specific wavelengths or any function of one or more of these statistics. In image processing language sets of metrics are also known as feature vectors. In addition, metrics can be derived from external considerations, such as embryo processing costs, embryo processing time, and the complexity of an assembly line sorting embryos by quality.

In another embodiment of the present invention embryo regions are scanned and spectral data is acquired regarding absorption, transmittance or reflectance of electromagnetic radiation (hereinafter referred to as light) at multiple discrete wavelengths ranging from 180 nm to 4000 nm. Differences in spectral data collected from embryos of high quality (for example, high conversion potential or high morphological similarity to normal zygotic embryos) versus those of low quality are presumed to reflect differences in chemical composition that are related to embryo quality. Numerous studies assert that embryo quality is related to gross chemical composition of the embryo or its parts, especially the amounts of water and storage compounds (proteins, lipids, and carbohydrates). Some examples include: Chanprame, S., T. M. Kuo, and J. M. Widholm, "Soluble Carbohydrate Content of Soybean [*Gycine max* (L.) Merr.] Somatic and Zygotic Embryos During Development," *In Vitro Cell Dev. Biol-Plant.* 34:64-68 (1998); Dodeman, V. L., M. Le Guilloux, G. Ducreux, and D. de Vienne, "Somatic and Zygotic Embryos of *Daucus carota* L. Display Different Protein Patterns Until Conversion to Plants," *Plant Cell Physiol.* 39:1104-1110 (1998); Morcillo, F., F. Aberlenc-Bertossi, S. Hamon, and Y. Duval, "Accumulation of Storage Protein and 7S Globulins During Zygotic and Somatic Embryo Development in *Elaeis Guineensis*," *Plant Physiol. Biochem.* 36:509-514 (1998);

and Obendorf, R. L., A. M. Dickerman, T. M. Pflum, M. A. Kacalanos, and M. E. Smith, "Drying Rate Alters Soluble Carbohydrates, Desiccation Tolerance, and Subsequent Seedling Growth of Soybean (*Glycine* mac L. Merrill) Zygotic Embryos During In Vitro Maturation," *Plant Sci.* 132:1-12 (1998).

Spectrometric analysis of embryos can be performed using a data collection setup that includes a light source, a microscope, a light sensor, and a data processor. Preferably, each embryo region undergoes multiple light scans in order to obtain a representative average spectrum. In addition, it is useful that the data processor include a built-in calibration program which is run periodically throughout the data collection phase to recalibrate the internal baseline to correct for dark current, and to recalibrate against the standard white background material upon which the embryo sits.

Preferably, the light sensor has a measuring interval of at the most 10 nm, preferably 2 nm, and most preferably 1 nm or less. The detection of light is performed in the ultraviolet, visible, and near infrared (including Raman spectroscopy) wavelength range of 180 nm to 4000 nm. This can be accomplished by the use of a scanning instrument, a diode array instrument, a Fourier transform instrument or any other similar equipment, known to the person of skill in the art.

The classification of embryos according to quality (as defined above) by the spectrometric measurements comprises two main steps. The first is the development of a classification model, involving the substeps of development of training and cross validating sets. Spectral data is acquired from embryos or embryo regions of known embryo quality, optionally a preprocessing of the acquired spectral data is performed, and then a data analysis is performed using one or more classification algorithms to develop a classification model for embryo quality. The second main step is the acquisition of spectrometric data from an embryo whose quality is unknown, optionally performing preprocessing of the acquired spectral data, followed by data analysis of the acquired spectral data using the classification model developed in the first main step.

Model training sets consist of a large number of absorption, transmittance or reflectance spectra acquired from embryos that have a known high or low quality. The training sets are used in the classification algorithms to develop a classification model. As previously noted, a variety of preprocessing algorithms are available that can be used to first reduce noise and adjust for base line drift. However, for some data sets it may not be necessary to preprocess the data to reduce background noise.

There are many data analysis methods that can be applied to develop and use classification models that allow plant embryos to be classified by quality. The above described mathematical methods are a sampling of some of the major techniques. However, it should be emphasized that data analysis techniques can be put together in an almost infinite number of combinations to achieve the desired results. For example, a soft independent modeling of class analogy (SIMCA) method can be used on images of embryos which have their color information collapsed into a single array using principal components and then the result can be shrunk using wavelets. SIMCA can then be used to build principal component regression models for each classification category. The Bayes optimal classifier can then be used to combine the classification decisions from six SIMCA model pairs. Partial least squares regression can be used in place of principal component regression in the SIMCA step. Similarly, neural networks can be used in place of Bayes optimal classifier to combine classification decisions into a final classification model.

In addition, the methods described for classifying plant embryos using embryo image data or absorption, transmittance or reflectance spectral data can be combined together in a number of different ways. For example, data analysis of the acquired raw visual and spectral data can be performed in parallel to develop a unitary classification model or the analysis can be conducted in series whereby two independent classification models are developed using the image and spectral data separately. Many permutations of the methods described herein are possible to accomplish the classification of plant embryos by embryo quality.

The following nonlimiting examples illustrate the inventive methods and the use of them to classify plant embryos that are most likely to be successfully germinated and produce normal plants.

Example 1

Mathematical Methods

There are three main steps in using light images to separate somatic embryos. They are: 1) cleaning the images to remove raw image data that is not from the plant embryo or embryo organ; 2) reducing the amount of raw image data acquired from the embryo or embryo organ while retaining as much embryo information as possible; and 3) applying one or more classification algorithms to develop and use a classification model for plant embryo quality.

Cleaning the Images

Image cleaning requires replacing the background in an image with zeros or pure black. The reason for this is to reduce variation between images. It is desired that the only differences between images be due to the embryos so that comparisons are not confounded with changes in the background. Since the images are magnified, slight variations in position, reflections, glints off leftover material from previous embryos are magnified and contribute to the differences between the images. Cleaning refers to the image processing steps used to eliminate all the variations in the background.

There is no set recipe for cleaning the embryo images since it is anticipated that as new imaging hardware and software are developed more suitable image cleaning technique will evolve. However, several techniques are generally useful. The examples described below are merely illustrative and are not meant to limit the present invention.

In the Examples that follow, the image of an embryo, its reflection on its stage and the remaining background were separated from each other using only the red component from the color image. The histogram of the red pixel values was positively skewed. A mixture distribution composed of three normal distributions was fit to the histogram by means of the EM algorithm. For a brief description of the EM algorithm see Mitchell, Tom M., *Machine Learning*, WCB/McGraw-Hill, pp. 191-196 (1997). The first normal picked up the background, the second normal picked up the reflection and the third component picked up the embryo. The mean of the second normal plus two times its standard deviation was used as the boundary between the reflection and the embryo. The red image was thresholded at this value. The resulting binary image still had some pixels that belonged to the reflection included in it. These were removed by using morphological operations on the binary image. Usually, one to three erosions followed by the same number of dilations are successful in cleaning up the image. Sometimes an extra couple of dilations were needed to restore the embryo part of the binary image to its proper size. Any holes in the embryo part of the binary image were then filled. The resulting binary image was then used to crop the color image and zero all non-embryo parts of the image. Each of the three color matrices in the original image were multiplied by the binary image and then cropped to within two pixels of the embryo. This method worked for all three views of the embryo.

Alternatively, a different method for cleaning each of the three embryo views can be used. In this alternative method the longitudinal top view of the embryo was preprocessed by first converting the red-green-blue values to hue. Saturation and intensity were not needed for this view. Taking the cotangent of $\frac{1}{255}^{th}$ of the hue flattened the range of the hue values making it easier to pick up more of the dark tail of the embryo. Only the positive hue values were used since most of the background ends up with negative or zero values for hue. Sometimes the positive hue values alone were enough. A binary image was created by thresholding the cotangent values at 100. Values above 100 were set to 1. One erosion followed by two dilations eliminated the spurious pixels from the background. The largest contiguous group of ones were kept as the embryo. Erosions and dilations were not done as many times as in the previous method, in order to keep the radical or tail portion of the embryo image attached to the main embryo body. Hole filling was done before the erosion and dilations in order to maintain the radical portion of the embryo image.

The longitudinal side view of the embryo (camera angle was rotated 90 degrees relative to the top view) was preprocessed by creating a matrix of maximum color values. The maximum color values at a pixel was the largest of the red, green, and blue color values. The maximum color values were used to ensure maximum retention of the embryo radical image. The embryo had a horizontal position in this image. Therefore, the row average was calculated from the maximum color values. The lowest average value between rows 200 and 260 corresponded to the gap between the embryo and the edge of the stage on which it sits. Everything below the row corresponding to the gap was set to zero. The rest of the image was thresholded so that values above ten were set to one. Again the binary image was eroded once and dilated twice to remove spurious pixels. A blob labeling routine labeled the remaining groups of pixels with values of ones and the largest one was kept as the embryo. If a second blob of ones had at least 25% of the number of pixels in it as the largest blob then the radicle was assumed to have been separated by the morphological operations and was included. Hole filling was done and then the binary image was used to zero the background parts of the original image and crop it as in the case of the top view.

The apical or end view of the embryo was preprocessed by one of two ways. The first method was to use the same method as described for the side view with three changes. After the stage part of the image was set to zero the remaining maximum values were thresholded at 20 instead of 10. The resulting binary image was eroded 3 times and dilated 5 times. Finally, no second largest blob was kept. The second method was to create a binary image from the product of two other binary images. The first binary image was created from the matrix of maximum values by setting all values greater than 20 to one and zero otherwise. The second binary image was made by creating a matrix of hue values as for the top view and then setting the positive values to one and all others to zero. The product of these two binary images eliminates almost all background features. The resulting binary image was eroded and dilated as in the first method. Finally, the binary image was used to zero the background and crop the original image as in the top view.

The reason the images were cropped was to concentrate later analytical effort on the embryo portion of the images as much as possible and to reduce the demands on computer memory. The three views of an embryo represented three correlated measurements of a single experimental unit. It took hundreds of thousands of numbers to describe the measurements. The embryo only covers about 5% of the total area of an image, so most of an image was background. Carrying along the background information needlessly uses up memory and can hamper later methods used to classify the embryos.

Image Reduction

Since embryo image data sets are often large, further image size reduction was performed in order to get the all of the data into computer memory. Also, the embryo classification algorithms that were used to sort the embryos required that all of the images of a particular embryo view be the same size. The sizes of the largest top view, side view and end-on view were found after all the images had been preprocessed and cropped as described in the preceding section. All top views were zero padded out to the size of the largest top view with the cotyledon embryo head placed as close to one of the corners of the image as possible. In other words, the extra zeros were added to the radicle end of the image and to one of the sides. Zero padding for the side and end views was similar. The zero padding scheme was performed in an effort to get all the embryo heads in the same place in the images, while the radical tail portion of the embryo, which is highly variable in size and shape, were left to occupy what ever image space they needed.

With the images of each embryo view reset to the smallest common size, the images were then shrunk using wavelet computational methods. The first step in reducing the images was to calculate the principal components of the red, green, and blue color matrices pixelwise. Each color matrix was strung out into a single long vector by appending the columns to each other. The first column was at the top of the vector and the last column was at the bottom. The red, green, and blue vectors were formed into a matrix with three columns and the singular value decomposition of this matrix was calculated. The left eigenvectors from the decomposition were principal components with unit length. The first eigenvector corresponded to the principal component that accounted for the most variation in the color values. On average the first principal component (PC) accounted for 95% of the variation. The first PC represents the optimal weighted average of the red, green, and blue values for explaining variation and is similar to a calculated grayscale value. The first eigenvector was then reshaped into a matrix and was used in place of the color array. This step reduced the computer memory requirements by ⅓ by replacing three matrices with a single matrix whose values were similar to a gray scale image. The single matrix carries all of the geometric information of the original. The second step was to do a two level two dimensional wavelet decomposition on the first PC image in order to reduce its size. The approximation coeffiecence[coefficient??] from the second level of the wavelet decomposition are used as the reduced image. The reduced image retains at least 75% of the variability in the original PC image.

Metrics

Reducing the image data using the aforementioned methods means that some of the information in the original color data is lost. In an attempt to keep some of this information, several statistics were calculated as the data reduction process was performed. First, the mean standard deviation, coefficient of skewness and coefficient of kurtosis were calculated for each color as well as hue, saturation and intensity. Next, the coefficients of the wavelet decomposition at each scale were summarized by their first five raw moments about zero. In a two level decomposition there are six matrices of detail coefficients and one of smooth coefficients. The detail coefficients contain information on texture. The first five raw moments about zero were estimated for each of these matrices as well as the smooth coefficients. The five moments about zero were the mean, mean squared value, mean cubed value, mean quartic value and mean quintic value. To obtain central moments like the variance, skewness, etc., one subtracts the mean from the individual values first. However, central moments were more similar for classification groups than for raw moments. A third set of statistics were calculated from the perimeter of the embryo and its wavelet decomposition and are intended to quantify shape information.

The perimeter of the embryo was traced in a clockwise direction and the row and column coordinates of the edge pixels were obtained. The pixel coordinates were interpolated to generate row and column vectors with 1024 elements in each. Because many of the embryo perimeters were concave curves, equiangular interpolation could not be used. Instead, linear interpolation was used to create 1024 equally spaced coordinates. The coordinates were mean centered and then radii were calculated from them. When plotted in sequence the radii formed a lumpy sinusoid. When plotted in polar coordinates they traced the embryo. A ten level wavelet decomposition was performed on the radii and the first seven raw moments about zero were calculated for each level. A similar method has been used by L. M. Bruce ("Centroid Sensitivity of Wavelet-based Shape Features," *Proceedings of SPIE, Wavelet Applications V*, Harold H. Szu, Editor, 3391: 358-366 (1998)) to classify breast tumors as cancerous or benign.

In addition to the moments of the wavelet coefficients from the radii, the area enclosed by the perimeter and it's length were calculated from the original coordinates. Also, the area and length of the convex hull of the perimeter were calculated. Lastly, the ratio of the perimeter area to the convex hull area and the ratio of the perimeter length to the convex hull length were calculated. If the embryo perimeter was a convex curve, then the last two ratios will be unity. Otherwise, the area ratio will decrease toward zero and the perimeter ratio will increase.

In all, 142 metrics were described for the above embryo images. These metrics were intended to capture some of the information on color, shape and texture that is lost when the somatic embryo images are reduced in size. Some of the information such as the perimeter shape information was still in the reduced images. Adding the metrics the classification model emphasizes the metrics information. In some analyses, (see Example 4, Tables 2 and 3) the logarithm of the metric is taken to reduce variability.

Embryo Classification Models
Principal Component Analysis/SIMCA

The primary classification method used in the Examples of the present invention was soft independent modeling of class analogy SIMCA. See Jolliffe, I. T., *Principal Component Analysis*, Springer-Verlag p. 161 (1986). SIMCA was used on each set of reduced images and metrics. This resulted in six intermediate classification of each embryo. These six intermediate classifications were combined using the Bayes optimal classifier. See Mitchell, Tom M., *Machine Learning*, WCB/McGraw-Hill pp. 174-176, 197, 222 (1997). SIMCA works by calculating a separate set of principal components for each category based on training data. The principal components which account for the majority of the variation are kept. Then data from a new sample is regressed on the principal components from each group. The residual mean square errors are calculated for each category. The category with the smallest residual mean square error is the category to which the new sample is assigned. Six SIMCAs are done for each embryo.

Combining the Intermediate Classifications Using the Bayes Optimal Classifier

Two to six or so intermediate classifications can be combined into a single classification rule by first converting the resulting strings of zeros and ones into a binary code. For two intermediate classifications there are four binary combinations, for three intermediate classifications there are eight binary combinations, and so on. For 'k' intermediate classifications there are $2^k$ binary combinations. Each binary combination is assigned a label or code. For each embryo quality class the probability of observing each code is estimated. Then the embryo-quality-class-by-binary-code probabilities are divided by the probability of the corresponding code occurring in all the data from both embryo quality classes. The resulting probabilities are the conditional probability of an embryo quality class given a code. An embryo's binary code is calculated and the embryo is assigned to the embryo quality class for which the conditional probability is highest for the observed binary code. Ties can be assigned randomly or assigned to one of the embryo quality classes based on other considerations such economics.

Using the Lorenz Curve for Classifying Embryos

Originally, the Lorenz curve was developed to compare income distribution among different groups of people. A Lorenz curve is created by plotting the fraction of income versus the fraction of the population that owns that fraction of the income. In the present invention, the Lorenz curve is viewed as a comparison of two paired cumulative distribution functions where the fractional values of one cumulative distribution function are plotted verses the fractional values of the second cumulative distribution function. If the two distributions are the same the Lorenz curve will plot the straight line $y=x$. The point farthest from the line $y=x$ corresponds to the balance point between accumulating more of one distribution than the other. The balance or extreme point is an objective point at which to separate the two distributions.

The Lorenz curve classification method of the present invention has four steps. First, Lorenz curves are calculated for each metric in a set of metrics. The points on these Lorenz curves the furthest from the line, $y=x$, are found. Second, the metric values corresponding to the extreme points on the Lorenz curves are used as the threshold values to make single metric classifications of the embryos: values of a metric less than its threshold are assigned to one embryo quality class and values greater than the threshold are assigned to the other embryo quality class. Third, the set of metrics is subsetted to reduce the number of combinations that must be searched in the final stage. Fourth, pairs, triples, quadruples, etc., of the single metric classifications are combined into binary codes and used in the Bayes optimal classifier to create classification models for assigning embryos to one of two quality classes. Classification models are made for all possible pairs, triples, quadruples, etc., and the best model is retained in each case.

Calculating the Lorenz Curve for a Single Metric

The metric values for the two embryo quality classifications are combined and all the distinct metric values identified. Alternatively, the minimum and maximum value of all the metric values for both embryo quality classifications combined are found and a user specified number of equally spaced steps between the minimum and maximum are used. When there are too many distinct values, this second option is useful. In either case, for each distinct metric value, the fraction of metric values less than or equal to the distinct value is recorded for each embryo quality class. Thus, two paired cumulative distribution curves are obtained. Plotting these two sets of fractions against each other constitutes the Lorenz curve. If the two distributions are the same, the Lorenz curve is the line, y=x.

Finding the Extreme Points on the Lorenz Curves

The distance of a point, $(x_0, y_0)$ from the line, y=x, is the absolute value of the difference between $y_0$ and $x_0$ divided by the square-root of two: $|y_0-x_0|/\sqrt{2}$. The absolute value of the difference between the cumulative distribution functions of the two classes of embryo quality for a metric is searched for its highest point. The corresponding metric value is used as the threshold. This extreme point is the balance point between one distribution accumulating more probability than the other distribution. The extreme point was used as the threshold in the metric classification models developed in Example 4. Other points on the Lorenz curve may be used as thresholds based on other considerations such processing costs. If a point other than the extreme point is used as the threshold, the Lorenz curve can be used to determine the tradeoff in missclassification error rates.

Single Metric Classifications

Metric values less than the threshold are assigned to one of the embryo quality classes and values greater than the threshold are assigned to the other quality class. These single metric classifications result in an embryo metric value being assigned a zero or one. This is done for each metric used, one embryo quality class is set to one and the other is set to zero. Several single metric classifications can then be combined to yield a final classification that has a lower misclassification error rate than any of the individual single metric classifications.

Combining the Lorenz Curve Single Metric Classifications Using the Bayes Optimal Classifier Two or more single metric classification models can be combined into a single classification rule using the same Bayes optimal classifier method previously described to combine intermediate SIMCA classification models. Alternatively, single metric classification models or intermediate SIMCA classification models can serve as the input data to neural network algorithm to arrive at a final classification model for plant embryo quality. However, as described below, when single metric classification models are combined to arrive at a final classification rule special problems arise.

Subsetting the Metrics to be Combined into a Single Classification Model

The Lorenz curve can be used to find an optimal threshold value for a single metric. Optimal is here defined in the sense of balancing probability accumulation. However, the Lorenz curve cannot handle the case when several metrics are considered together because the Lorenz curve can only compare two distributions at a time. One solution is to feed sets of metrics into an artificial neural network to find an optimal classification rule. However, with hundreds of metrics, it would be necessary to either fit very large networks or fit a very large number of small networks. For the purpose of this application, the simpler the classification rule the better. It is recognized that the thresholds found for individual metrics may not be the best ones to use when combining several metrics through their single metric classifications. Nevertheless, it is possible to search large numbers of combinations of single metric classifications by calculating the results of the Bayes optimal classifier approach outlined above and comparing them for various combinations of the single metric classifications. Yet there are still limitations on the number of combinations that can be searched. When there are 682 metrics being considered, then there are 8.935 billion distinct four-metric combinations alone. As computers get faster such a number will not pose much of a problem. However, for limited computing hardware, subsetting the metrics will greatly reduce the amount of work.

Two subsetting criterion present themselves. First, the metrics whose single metric classifications are above some limit can be kept. Second, many of the metrics are correlated with each other. The metrics highly correlated with the better metrics can be dropped from consideration since they are informational twins to the better metrics: a metric perfectly correlated with another contains no information not already in the other metric. Metrics with very low correlations among them are more likely to create useful binary codes. These subsetting criterion can be used together to reduce the number of metrics.

Several different examples of classification techniques are specifically demonstrated in the Examples 2-4.

Example 2

Somatic Embryo Sorting Based Upon Visual Embryo Quality

Douglas-fir somatic embryos were cultured to the cotyledon stage by the methods outlined in Gupta et al., U.S. Pat. No. 5,036,007, and Gupta, U.S. Pat. No. 5,563,061, which patents are herein incorporated in their entirety by reference. Embryos were individually removed from the development stage medium. From this point they would normally be manually screened and selected for germination.

In the present case, two hundred embryos from the same clone of Douglas-fir genotype 5 were preselected by morphology using the usual zygotic embryo criteria of color, axial symmetry, freedom from obvious flaws, and cotyledon development. Half of the sample was considered to be "good" embryos; i.e., embryos that met visual criteria for further processing in germination medium. The other half were "bad" embryos that did not meet the criteria, The "truth criterion" for the following analysis was the presence or absence of normal zygotic-like morphology.

After selection, the embryos were placed against a dark background and illuminated by cool fiber optic light. Each embryo was individually color-imaged in rapid sequence by three cameras mounted perpendicular to each other. Two longitudinal views 90° to each other and an apical end-on view of the cotyledon region were acquired. Images were acquired as digitized data suitable for computer analysis. Prior to analysis the images were preprocessed to isolate the embryo and thus eliminate interfering background data.

In this example, a subset of the embryo top view images were used to calculate the principal components. The first 80 components were kept as they account for about 98% of the variation in the images. Principal components were calculated for the "good" embryos, i.e., those embryos that possess good visual criteria that are associated with a high germination rate, as well as for embryos that lack the good visual features. The principal components were calculated using the singular value decomposition algorithm. The singular value decomposition algorithm is available with any software capable of handling matrices. The principal components used were the left eigenvectors from the singular value decomposition which were the principal components normalized to have unit length. This normalization process does not have an adverse effect because the principal components were being used in this method as a set orthogonal basis vectors in a multiple regression. The embryos that were not included in the training data set were then regressed on the two sets of principal components exactly as done in multiple regression. For each regression the residual mean square error was calculated. A test embryo was classified as having either good or bad embryo visual quality depending on which category has the smaller residual mean square error. Using this method test embryos were classified based on the longitudinal top view of an embryo.

Similar to the longitudinal top view images, the longitudinal side view and end view images were divided into a training set and test set of embryos. The training set of embryos were used for calculating the principal components and the test set of embryos were regressed on them and classified. Likewise, the metrics were used to calculate principal components and classify the embryos in the test set. In the case of the metrics, 40 principal components were kept and they were based on the natural logarithm of the absolute value of the metrics multiplied by the sign of the metric or the Box-Cox transformation (Myers, R. H. and D. C. Montgomery, *Response Surface Methodology: Process and Product Optimization Using Designed Experiments*, Wiley, pp. 260-264 (1995)) of the metrics using an odd root such as a $1/101$ which approximates the natural logarithm, preserves the sign, and still works on zero. The transformation helps reduce the variability of the higher order moments. As a result each embryo in the test set ends up with six classifications from each of the SIMCAs: three classifications from the three images and three classifications from the three sets of metrics.

The six classifications were combined into a single classification using Bayes optimal classifier as follows. See Mitchell, T. M. *Machine Learning*, WCB/McGraw-Hill, pp. 174-176, 197, 222 (1997). Each classification was either zero or one: one meaning that the embryo had a good visual quality and zero meaning that the embryo did not have good visual characteristics. These six binary classification scores were converted to a multi-valued code by multiplying the side view image score by 32 and adding it to 16 times the end view image score plus 8 times the top view image score plus 4 times the side view metric score plus 2 times the end view metric score plus the top view metric score. This composite score takes on integer values ranging from 0 to 31. For each composite score, the number of good visual quality embryos were counted as well as the number of bad visual quality embryos. Dividing by the total number of embryos in the test set yields the probabilities of observing each score and one of the embryo categories. The probability of each composite score occurring was calculated by counting how many times each score occurred and dividing by the total number of embryos in the test set. Next, each probability of observing a composite score and one of the categories was divided by the probability of the composite score occurring. This calculation gave the probability of a category given a composite score. Composite scores where the probability of observing a visually correct embryo was greater than or equal to 50% were assigned as having a good embryo quality. All other scores were assigned to the bad embryo quality category. In this way the information from the six SIMCA classifications were combined into a single classification.

Basically, the Bayes optimal classifier assigns a composite score to the category which generates the most of that particular score. If an embryo has a value that is in the middle it was put into the good embryo quality category. The whole process was repeated many times and the average performance reported.

Using the above methods two additional sets of somatic embryos of two different genotypes (genotypes 6 and 7) were classified as having good or bad morphological qualities as compared to normal zygotic embryos. The results of the three sets are given in Table 1.

TABLE 1

Visual Quality Classification Results From the Bayes Optimal Classifier for Three Genotypes of Douglas-Fir Somatic Embryos

| Douglas-fir Genotype | Percent of Embryos Classified Correctly as Having "Good" Visual Embryo Quality | Percent of Embryos Correctly Classified as Having "Bad" Visual Embryo Quality |
|---|---|---|
| 5 (Three views of 200 embryos) | 80.0 | 75.0 |
| 6 (Three views of 1000 embryos) | 88.7 | 70.5 |
| 7 (End & Top views of 1000 embryos) | 87.0 | 78.5 |

Example 3

Somatic Embryo Sorting Based Upon Visual Embryo Quality and Actual Germination

A sample of 400 embryos judged to be of high morphological quality, as previously defined, from the Douglas-fir genotype 5 was evaluated in two ways. After evaluation the embryos were germinated to determine whether germination success correlated with predicted success based on eight additional morphological features. The base case was visual selection based on morphology. The first procedure was a nonparametric statistical treatment based on four observed features (symmetry, surface roughness, presence of fused cotyledons, and presence of gaps between cotyledons) and four measured embryo dimensions (hypocotyle length, radical length, cotyledon length, and cotyledon number) the measurements being made on digital color images acquired under sterile conditions from a single viewpoint perpendicular to the long axis of the embryo. This statistical procedure is known as binary recursive classification and was carried out using software named CART™ (for Classification and Regression Tree) (Salford Systems, San Diego, Calif.). Reliability of this classification method was assessed and probabilities for future similar data sets were derived by validating the classification on a specified number; e.g., 20, random subsets of the data. CART™ classification is binary and all possible splits were tested on all variables. The second evaluation method was principal components analysis of the images.

Results showed principal components analysis was superior to the CART™ statistical procedure and was a major improvement over technician selection. A 66.3% germination rate was found for the base populations (selected for good similarity to normal zygotic embryos). This improved to 75.0% for embryos classified by the CART™ procedure as most likely to germinate. A germination success of 79.7% was achieved in embryos chosen by the principal components/SIMCA analysis method.

Example 4

Somatic Embryo Sorting Based Embryo Germination

A Comparison of Classification Methods

The methods in Examples 1-3 were used to develop classification models and classify 1000 somatic embryos of Douglas-fir genotype 6 by their capability to germinate. Table 2 contains the results of presenting different inputs to the Bayes optimal classifier when classifying the germination versus nongermination capabilities of the Douglas-fir genotype 6 embryos. When the data input was somatic image data that was first preprocessed using the method of Example 1 the training set model for the classification of embryos by germination was accurate 59% of the time at correctly classifying embryos as embryos that would germinate and about 64% accurate at classifying embryos that would not germinate. This is an average accuracy of 61.7%. In contrast, when metrics image data was captured and added to the preprocessed image data following the methods in Example 1, the accuracy of embryo classification into germinating and non-germinating embryos was increased to about 71% (column 4 of Table 2). Thus, as in Example 2, an increased accuracy in classifying potential germinants was achieved using the present invention.

TABLE 2

Germination Classification of Douglas-Fir
Genotype 6 Somatic Embryos
Using Different Inputs to Bayes Optimal Classifier
Compared With Germination Results
of Manual Selection Based on Morphology

| Combinations of SIMCA Results Used in Bayes Optimal Classifier | Percent of Germinating Embryos Correctly Classified as Germinating | Percent of Non-Germinating Embryos Correctly Classified as Non-Germinating | Average Success in Classifying Correctly |
|---|---|---|---|
| Images Only | 59.3 | 64.1 | 61.7 |
| Images + Metrics | 67.6 | 74.6 | 71.1 |
| Images + Log (Metrics) | 68.5 | 74.1 | 71.3 |
| Manual Selection Based on Morphology | 71.7 | 66.2 | 68.9 |

Table 3 presents the germination classification results for Douglas-fir genotype 6 of the individual SIMCA runs from each set of images and metrics of the somatic embryos. Comparing the results presented in Table 3 with those shown in Table 2 demonstrates the statistical advantage of combining the individual SIMCA classifications using the Bayes optimal classifier of each of three different somatic embryo views. Also, the utility of adding the metrics is illustrated.

TABLE 3

Germination Classification of Douglas-Fir
Genotype 6 Somatic Embryos:
Results From the Individual SIMCA Runs

| Data Used | Percent of Germinating Embryos Correctly Classified as Germinating | Percent of Non-Germinating Embryos Correctly Classified as Non-Germinating |
|---|---|---|
| Top View Images | 66 | 54 |
| Top View Log(Metrics) | 46 | 63 |
| End View Images | 70 | 45 |
| End View Log(Metrics) | 52 | 52 |
| Side View Images | 48 | 59 |
| Side View Log(Metrics) | 52 | 53 |

Additional Classification Methods

Two additional classification methods were performed with data collected from somatic embryos: neural networks (Douglas-fir genotype 6) and a classification method based on the Lorenz curve (Douglas-fir genotypes 6 and 7). The method based on SIMCA uses hyperplanes as boundaries between categories. A two dimensional hyperplane is a line and a three dimension hyperplane is a regular plane or flat surface. In short, hyperplanes are just higher dimensional cousins to lines and regular planes. As a result they are best for separating categories that are linearly separable, i.e., they have straight boundaries and can be separated by a "line". Often nature does not have linear boundaries but very curved boundaries. Simple back-propagation neural networks using nonlinear transfer functions for the hidden nodes and output nodes can handle very nonlinear boundaries between categories. See Hagan, M. T., H. B. Demuth, and M. Beale, *Neural Network Design*, PWS Publishing Company, Chapters 11 and 12 (1996). These have been used to discriminate between images of people looking in different directions. Id. pp. 112-115.

Neural Network

Back-propagation neural networks were used to classify embryos of genotype 6 as germinating or non-germinating. The end view and top view somatic embryo images were reduced in size by wavelets in order to reduce the number of network input nodes as was suggested by T. M. Mitchell (*Machine Learning*, WCB/McGraw-Hill, pp. 112-115 (1997)). Mitchell used adjacent averages to reduce his images. Here the smooth coefficients from the $3^{rd}$ level of the two-dimensional wavelet decomposition were used since they preserve much more detail than averages. The embryo side view was not included to reduce the amount of computation and because as shown in Table 3 this view carries the least amount of information about germination of three views. The input layer of the network just fed in the pixel values from the reduced images from both views. The hidden layer had either 18 or 80 hidden nodes using the logistic transfer function, $1/(1+\exp(-x))$. The output layer had two nodes again using logistic functions. The output target values were (0.9, 0.1) for germinating somatic embryos and (0.1, 0.9) for non-germinating embryos. The sum of the squared differences between the target vectors and their predicted vectors were minimized. Half the data was used for training and half was used for validation. Any training set and even all of the embryos could be perfectly classified with the 18 hidden node model. The best either of the neural network models could do on a validation or test set was 61% correct classification of embryos into both the germinating and non-germinating classes.

Use of the Lorenz Curve Classification Method to Classify Embryos

As previously noted the Lorenz curve classification method has four steps. In this example, 625 and 457 different metrics were calculated for Douglas-fir genotypes 6 and 7, respectively. Metric values corresponding to the extreme points on the Lorenz curves for each metric were set as threshold values for classifying embryo quality. In addition, the set of single metric classifications which were searched for robust combination classification models was reduced using the subsetting routine described in Example 1. Lastly, double, triple, quadruple, etc., combinations of the single metric classification models were combined into binary codes and used in the Bayes optimal classifier to create classification rules for assigning embryos to one of the two embryo quality classes. Classification models were made for all possible pairs, triples, and quadruples and the best model was retained in each case.

Table 4 contains the results of classifying embryos according to their morphological similarity to normal zygotic embryos by using the Lorenz Curve classification method combining 1, 2, 3, and 4 single metric classifications via the Bayes optimal classifier.

TABLE 4

Morphology Classification Results From the Best Bayes Optimal Classifier Combining 1, 2, 3 & 4 Lorenz Curve Single Metric Classifications for Douglas-Fir Genotypes 6 and 7

| Douglas-fir Genotype | Number of Metrics Used to Create Classification Model | Percent of Good Morphology Embryos Correctly Classified as Having Good Morphology | Percent of Bad Morphology Embryos Correctly Classified as Having Bad Morphology |
| --- | --- | --- | --- |
| 6 (end, side & top views) | 1 (Skewness coefficient, $\beta_1$, of all the intensity pixel values from the embryo end view) | 82.30 | 70.44 |
| 6 (end, side & top views) | 2 (Skewness coefficient, $\beta_1$, of all the intensity pixel values from the embryo end view, and Range of the perimeter radii from the embryo end view) | 72.63 | 83.27 |
| 6 (end, side & top views) | 3 (Skewness coefficient, $\beta_1$, of all the intensity pixel values from the embryo end view, range of the perimeter radii from the end view, and standard deviation of the area of the cotyledons from the embryo end view) | 79.69 | 78.96 |
| 6 (end, side & top views) | 4 (Skewness coefficient, $\beta_1$, of all the intensity pixel values from the embryo end view, range of the perimeter radii from the end view, standard deviation of the area of the cotyledons from the embryo end view, and mean area of the cotyledons touching the bounding convex hull of the embryo end view) | 84.72 | 75.75 |
| 7 (end & top views only) | 1 (Lower quartile of the perimeter radii from the embryo top view) | 88.59 | 71.61 |
| 7 (end & top views only) | 2 (Lower quartile of the perimeter radii from the embryo top view | 71.33 | 89.74 |

TABLE 4-continued

Morphology Classification Results From the Best Bayes Optimal Classifier Combining 1, 2, 3 & 4 Lorenz Curve Single Metric Classifications for Douglas-Fir Genotypes 6 and 7

| Douglas-fir Genotype | Number of Metrics Used to Create Classification Model | Percent of Good Morphology Embryos Correctly Classified as Having Good Morphology | Percent of Bad Morphology Embryos Correctly Classified as Having Bad Morphology |
|---|---|---|---|
| | and skewness coefficient, $\beta_1$, of the blue pixel values from the embryo end view) | | |
| 7 (end & top views only) | 3 (Skewness coefficient, $\beta_1$, of all the blue pixel values from the end view, standard deviation of all the green pixel values from the end view, and $4^{th}$ moment about zero of the detail coefficients of the $8^{th}$ level of a 10 level wavelet decomposition of the embryo end view perimeter) | 85.71 | 84.97 |
| 7 (end & top views only) | 4 (Skewness coefficient, $\beta_1$, of all the blue pixel values from the end view, standard deviation of all the green pixel values from the end view, $4^{th}$ moment about zero of the detail coefficients of the $8^{th}$ level of the wavelet decomposition of the end view perimeter, and lower quartile of the perimeter radii from the embryo top view) | 85.10 | 87.05 |

Comparing the results in Table 4 with the corresponding results in Table 1 from combining 6 SIMCA intermediate classifications by the Bayes optimal classifier suggests that the Lorenz curve based method performs as well as or better than the SIMCA based method for classifying embryos according to morphology. Similarly, Table 5 contains the results from classifying embryos according to germination classes by the Lorenz curve method. Comparing Table 5 with Table 2 shows that the Lorenz curve method does not perform as well as the SIMCA based method. Also, Table 4 and Table 5 show that combining the information in multiple metrics reduces the misclassification error rate.

TABLE 5

Germination Classification Results From the Best Bayes Optimal Classifier Combining 1, 2, 3 & 4 Lorenz Curve Single Metric Classifications for Douglas-Fir Genotype 6

| Douglas-fir Genotype using (end, side & top views) | Number of Metrics Used to Create Classification Model | Percent of Germinating Embryos Correctly Classified as Germinating | Percent of NonGerminating Embryos Correctly Classified as NonGerminating |
|---|---|---|---|
| 6 | 1 (Skewness coefficient, $\beta_1$, of all the blue pixel values from the embryo end view) | 70.51 | 60.12 |

TABLE 5-continued

Germination Classification Results From the
Best Bayes Optimal Classifier
Combining 1, 2, 3 & 4 Lorenz Curve Single
Metric Classifications for Douglas-Fir
Genotype 6

| Douglas-fir Genotype using (end, side & top views) | Number of Metrics Used to Create Classification Model | Percent of Germinating Embryos Correctly Classified as Germinating | Percent of NonGerminating Embryos Correctly Classified as NonGerminating |
|---|---|---|---|
| 6 | 2 (Skewness coefficient, $\beta_1$, of all the blue pixel values from the embryo end view, and $10^{th}$ level detail coefficient from a 10 level wavelet decomposition of the embryo side view perimeter) | 66.51 | 65.45 |
| 6 | 3 (Skewness coefficient, $\beta_1$, of all the blue pixel values from the embryo end view, kurtosis coefficient, $\beta_2$, the perimeter radii from the embryo top view, and mean of the level 9 detail coefficients from a 10 level wavelet decomposition from the embryo side view perimeter) | 71.56 | 62.40 |
| 6 | 4 (Skewness coefficient, $\beta_1$, of all the blue pixel values from the embryo end view, kurtosis coefficient, $\beta_2$, the perimeter radii from the embryo top view, mean of the level 9 detail coefficients from a 10 level wavelet decomposition from the embryo side view perimeter, and kurtosis coefficient, $\beta_2$, of all the green pixel values from the embryo side view) | 65.33 | 70.70 |

Classification Trees Based on the Lorenz Curve

An alternative method for classifying embryos uses Lorenz curve as the method for splitting nodes in classification trees. Usually to construct a classification tree the metrics are searched to find a variable that separates the quality classes the most based on a measure of distance or spread. Multivariate statistics can also be used to examine sets of metrics, however, the computation required increases rapidly with the number of metrics in a set. The Lorenz curve method outlined above can also be used as a node splitting criterion. The Lorenz curve method outlined above was used to search for a single best metric to split the embryo quality classes. The two subsets thus created were each submitted to the Lorenz method to find a metric that best split them. This process can be repeated as long as the number of metric values from each embryo quality class are large enough to provide a good estimate of the distribution functions. The entire set of metrics is searched each time because the act of splitting the distributions, alters the distributions, and metrics that at first provided poor separation may provide good separation at later stages. This method of method of creating a classification tree is very computationally intensive. As a result the metrics can be subsetted in order to get the computations done in a reduced time. A two level classification tree based on the Lorenz curve was created for Douglas-fir genotype 7. The results are in Table 6.

TABLE 6

Morphology Classification Results From a
Two Level Classification and Regression Tree Using
Lorenz Curves to Split Nodes for Douglas-Fir Genotype 7

| Douglas-fir Genotype 7 using (end & top views only) | Number of Metrics Used to Create Classification Model | Percent of Good Morphology Embryos Correctly Classified as Having Good Morphology | Percent of Bad Morphology Embryos Correctly Classified as Having Bad Morphology |
|---|---|---|---|
| | 2 (Standard deviation of all the red pixel values from the embryo end view, and $2^{nd}$ moment about zero of all the pixel values in the $1^{st}$ principal component image (the view created by collapsing the red, green, and blue color matrices into a single matrix using principal components) of the end view) | 81.22 | 82.25 |

The techniques described in Examples 1-4 can be readily adapted to continuous examination of somatic embryos as might be required in a large scale production facility. In addition, these methods can be combined in series with themselves or with the spectroscopy methods described in Example 5 to create an efficient and cost effective screening methodology for classifying somatic embryos by their germination potential.

Example 5

Spectrophotometric and Multivariate Methods for Classifying Somatic Embryos

Spectral data was collected and analyzed from zygotic and somatic embryos populations that from experience are known to differ considerably in germination vigor.

Zygotic Embryos

Fresh zygotic embryos were collected at two intervals about three weeks apart from one orchard grown Douglas-fir tree (*Pseudotsuga menziesii*). The degree of embryo development corresponded to Stages 7 and 8a in the classification published by Pullman et al. (Pullman, G. S. and D. T. Webb, "An Embryo Staging System for Comparison of Zygotic and Somatic Embryo Development," *Proc. TAPPI* [Technical Association of the Pulp and Paper Industry] Biological Sciences Symposium, Minneapolis, Minn., Oct. 3-6, 1994, pp. 31-33. TAPPI Press, Atlanta, Ga. (1994)) for the July 23 and August 13 collections, respectively. These stages may be described as "just cotyledonary" and "cotyledonary, immature." In addition, fully mature zygotic embryos were obtained from mature seed obtained from a seed store collected from a mix of different trees grown in the same orchard. Immature loblolly pine (*Pinus taeda*) zygotic embryos were collected from one tree on August 10, at which date they were at Stage 7 in Pullman et al.'s classification system cited above. Mature loblolly pine seed embryos were obtained from freezer storage, and the decoated seed allowed to imbibe water for 14 hours before extraction of the embryos for analysis. Cones and seed were stored at 4-6° C. after collection until spectral analysis was performed.

Somatic Embryos

Douglas-fir somatic embryos of four different genotypes, designated 1, 2, 3, and 4, were analyzed in this study. The Douglas-fir somatic embryos were cultured as described in Example 2. Where a cold treatment is noted, the Douglas-fir somatic embryos received cold treatment at 4-6° C. for four weeks prior to spectral analysis. Two genotypes of loblolly pine somatic embryos were used in the study, designated genotypes 5 and 7. After completing their development to the cotyledonary embryo stage on petri plates, half of the somatic loblolly pine embryos from each genotype received a partial drying treatment for 10 days at about 97% relative humidity while still on the culture medium, followed by cold treatment at 4-6° C. for four weeks. The other half of the loblolly somatic embryos did not receive this treatment. The loblolly somatic embryos were produced using standard somatic embryo plating methods described in Gupta et al., U.S. Pat. No. 5,036,007 and Gupta, U.S. Pat. No. 5,563,061.

For each population, spectral analysis was performed on about 10 embryos except for some somatic embryos where spectral data was collected from about 15-40 embryos. Spectra were taken usually from the cotyledon region of an embryo (FIG. 1). However, it should be understood that the inventive method can be practiced by collecting spectral data from the entire embryo or from the hypocotyl (12) or radical (14) portions of the embryo as diagrammed in FIG. 1. In some instances the classification was improved by using both cotyledon (10) and radical (14) data in sequence.

Collection of Spectral Data

The experimental setup consisted of a light source, a binocular microscope, a NIR sensor, and a portable NIR processor with computer. A FieldSpec FR (350-2500 nm) Spectrometer (Analytical Spectral Devices, Inc., Boulder, Colo.) equipped with a fiber optic probe which gathers light reflected from any surface was used to collect embryo spectral data. The fiber optic probe of the spectrometer was fitted with a 5 degree fore-optic and inserted into the auxiliary observation (camera) port of a binocular microscope.

Spectra were acquired sequentially from groups of ten somatic embryos immediately after hand-transferring from a culture plate, and from zygotic embryos on a one-by-one basis immediately after excision from decoated seeds using the apparatus and procedures described below. The halogen lamp was set at 40 degree angle from the vertical at a distance of 17 cm from the embryos. Samples were placed on a white Teflon surface to minimize background absorption while being viewed with the 6.5×, 10×, or 40× microscope objective. A "white balance" program that is part of the spectrometer, was run periodically throughout the measurements to recalibrate the instrument against the white background when no embryos were present.

Spectra were measured in the region from visible to very near IR range (350 to 2500 nm). Spectral intensities were measured at 1 nm increments. The spectrometer was programmed to complete 30 spectral scans of each embryo in order to obtain a representative average spectrum—a process which took a total of 30 seconds per embryo for separate cotyledon and radical sampling, including the time to reposition for the next embryo.

Data Processing and Information Extraction

Analysis of spectral data was performed using a Principal Component Analysis software package ("The Unscrambler" by Camo ASA, Oslo, Norway). The scores and loadings matrices were converted to the "scoreplots" and "loadings spectra" shown in the figures. The principal component analysis algorithm extracted the best set of axes that described the data set. The scoreplots show the relationships among the embryos, and embryo classes, while the loadings spectra show which spectral features were responsible for the class distinctions.

Principal Component Analysis of Spectra From Zygotic and Somatic Embryos

A comparison of Douglas-fir zygotic embryos of three different developmental stages and somatic embryos from Genotype 1 was performed. The three zygotic stages consisted of two immature cotyledonary stages, identifiable as stages 7 and 8 in Pullman et al. (Pullman, G. S. and D. T. Webb, "An Embryo Staging System for Comparison of Zygotic and Somatic Embryo Development," *Proc. TAPPI* [Technical Association of the Pulp and Paper Industry] Biological Sciences Symposium, Minneapolis, Minn., Oct. 3-6, 1994, pp. 31-33. TAPPI Press, Atlanta, Ga. (1994)) collected from the field in Rochester, Wash., on July 23 and August 14, respectively, and mature dry seed from a seedstore. Previous data showed that whereas 90-95% of the mature-seed embryos would germinate normally in vitro, only about 75% and 43% of the stage 8 and stage 7 embryos respectively would so germinate. The rates of shoot and root elongation— measures of germination vigor—had even greater sensitivity to developmental stage, these rates being reduced to 80% and 20% for the two immature stages. Germination was reduced to about 15% and zero, respectively, for the two immature stages after desiccation of the embryos to 10% moisture content. These data exemplify, for Douglas-fir, the large contrast in embryo quality between embryos at these stages of development, which is well-known to those skilled in plant embryo development. In further contrast, quality of the somatic embryos, which were closest, but not truly equivalent to, zygotic developmental stage 8, was characterized by significantly lower germination normalcy and vigor than the stage 7 zygotic embryos. The genotype tested was representative of many somatic embryo genotypes.

Figure 2A:
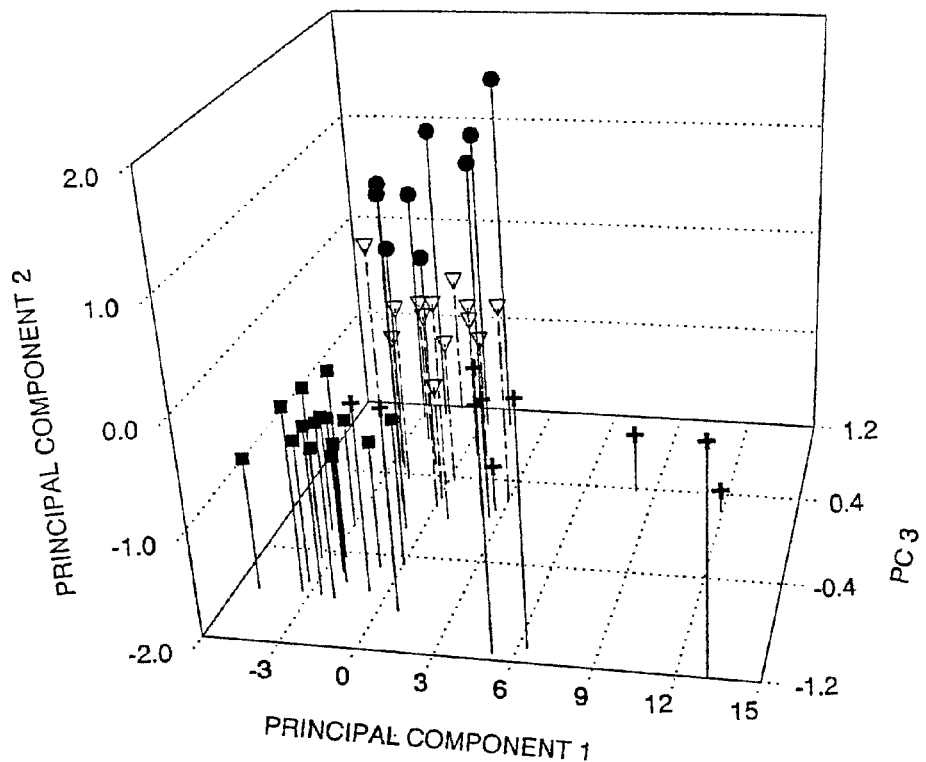
FIG. 2A displays a scoreplot obtained from principal component analysis of spectral data collected from Douglas-fir zygotic embryos of three different developmental stages and a set of Douglas-fir somatic embryos (genotype 1). The units on the principal component (PC) axes are universal standard deviations for the set.

Inspection of the scoreplot in FIG. 2A shows that these four populations of contrasting embryo quality separate into four clearly distinct groups when plotted with respect to the first three principal components. The embryo groups are: mature dry zygotics (black circles), August 14 zygotics (inverted white triangles), July 23 zygotics (black squares) and genotype 1 somatics ("+" symbol). The centroid of the somatic embryo group was shifted 8-10 standard deviations to the right along the PC1 axis compared with all stages of zygotic embryos, which were separated primarily along the axes for PCs 2 and 3. Variability within the somatic embryos was much greater than within any of the zygotic embryo groups.

Figure 2B:
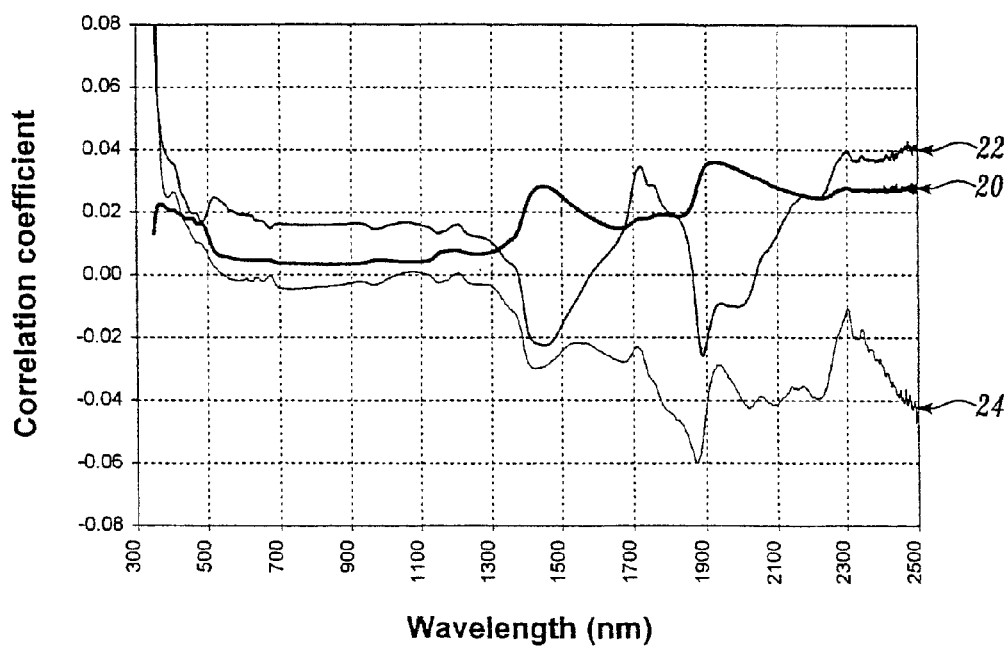
FIG. 2B shows the loadings spectra for each PC depicted in FIG. 2A. Each curve shows the relative contribution that each wavelength makes in accounting for the variance depicted along the scoreplot axes in FIG. 2A.

The loadings spectrum for PC1 (FIG. 2B, curve 20) contained mainly two peaks, at 1450 and 1920 nm, attributable to water, indicating that the large separation and variability was due to a greater amount and variability of somatic embryo water. In contrast, separation among the zygotic groups was mainly along PCs 2 (curve 22) and 3 (curve 24), whose loadings spectra suggest a basis in greater lipid content (the double peak at 1720-1750 nm, and the peak at 2300 nm) for more mature embryos. Also, there are negative peaks around 1400 and 1900 nm that may have to do with hydrogen-bonded water. The somatic embryos were also separated from the two more mature zygotic groups along the PC2 axis, due in part to their putative lower lipid concentration, as well as absorption differences in the visible region. The percent of total spectral variation accounted for by each PC was 84% for PC1, 8% for PC2, and 4% for PC3. Table 7 summarizes the quality of separation obtained among the four embryo groups after principal component analyses of the spectral data. The summary data tables for the various somatic embryo classifications list the chemical features that are inferred to be associated with specific wavelengths based upon the known spectrophotometric behavior of that chemical class.

TABLE 7

Douglas-Fir Zygotic Embryos at Three Developmental Stages Compared With One Another, and With Somatic Embryos

| Immature Zygotic Embryos | | | | Principal | Wavelength/Inferred |
|---|---|---|---|---|---|
| Stage 7 embryos | Stage 8 embryos | Mature Seed Embryos | Somatic Embryos | Components Needed | Chemical Features Involved |
| 15/15* | 14/14* | 8/9* | 9/10* | 1st | Water (1450 nm + 1920 nm) |
| (100%) | (100%) | (89%) | (90%) | 2nd | Lipid (1700-1750 nm) |
| | | | | 3rd | Lipid + feature at 1890 nm |
| | | | | | Lipid (2300 nm) + feature at 1870 nm |

*Number correctly classified/number tested

TABLE 8

Loblolly Pine Zygotic Embryos at Two Developmental Stages and Loblolly Pine Somatic Embryos

| Immature (stage 8) Zygotic Embryos (Aug. 10) | Mature Zygotic Embryos (October) | Somatic Embryos | Principal Components Needed | Wavelength/ Inferred Chemical Features Involved |
|---|---|---|---|---|
| 10/10* (100%) | 13/13* (100%) | 28/29* (97%) | 1st | Water (1450 + 1920 nm) |
| | | | 2nd | Lipid (1700-1750 nm) |
| | | | 3rd | 1800 nm broad peak |
| | | | | Lipid (-ve 2300 nm) |
| | | | | Protein (1210 nm) |
| | | | | Lipid (1700-1750 nm) |
| | | | | Pigments (400-500 nm) |

*Number correctly classified/number tested

Figure 3A:
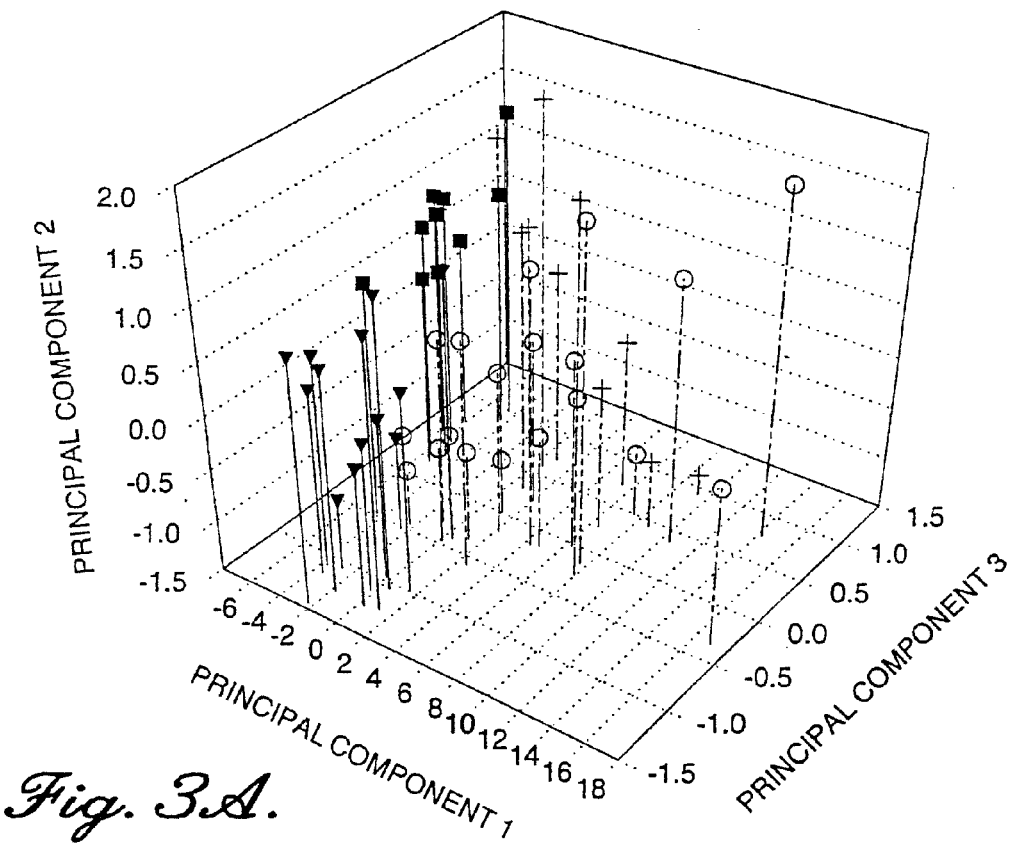
FIG. 3A displays a scoreplot obtained from principal component analysis of spectral data collected from loblolly pine zygotic embryos of two different developmental stages and two sets of somatic embryos (genotypes 5 and 7). The units on the PC axes are universal standard deviations for the set, and the crossover of zero axes is the average behavior of all the embryos.
Figure 3B:
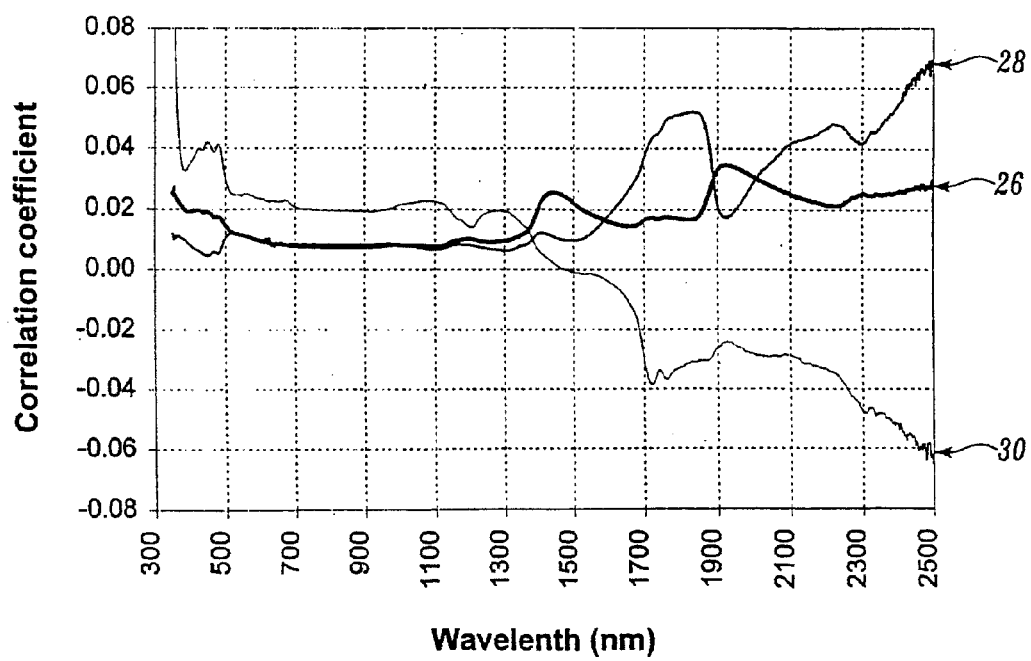
FIG. 3B shows the loadings spectra for each PC depicted in FIG. 3A. Each curve shows the relative contribution that each wavelength makes in accounting for the variance depicted along the scoreplot axes in FIG. 3A.

The results with loblolly pine somatic and zygotic embryos are shown in FIG. 3A and Table 8. In this case, stage 8 zygotic embryos (black squares) and water-imbibed mature zygotic embryos (black triangles) are compared with two genotypes of somatic embryos (genotype 5 denoted as "+" and genotype 7 denoted as "o") pretreated by partial drying then cold. Somatic embryos were separated from zygotic embryos mainly by PC1, which, as in case of Douglas-fir embryos, was probably due to the somatic embryos' higher water content relative to lipids (curve 26). Also, many loblolly pine somatic embryos were separated from zygotic embryos along PC2, which featured a dominant broad peak around 1800 nm of unknown source (curve 28). PC3 further distinguished the mature imbibed zygotic embryo group from the somatic embryo group, based on a combination of features, including a lipid (-ve) peak, pigmentation in the visible region, and a small -ve peak around 1210 nm (which is about where the second overtone of C-H stretches in protein lie) shown in curve 30. Together, these three PCs accounted for 97% of variation in the spectra (FIG. 3B). The percent of total spectral variation accounted for by each PC was 92% for PC1 (curve 26), 4% for PC2 (curve 28), and 1% for PC3 (curve 30).

Taken together, these data demonstrate that embryos can be accurately separated by their NIR spectral characteristics into groups of differing germination potential.

Principal Component Analysis of Spectra From Somatic Embryos of High- and Low-Quality Appearance Ten cotyledonary-stage somatic embryos of high- and low-quality appearance were selected from a single plate each of Douglas-fir (genotype 2) and loblolly pine (genotype 5) embryos, based upon traditional morphological indications of embryo quality, i.e., morphologies that are most likely to result in a high or low frequency of germination.

Figure 4A:
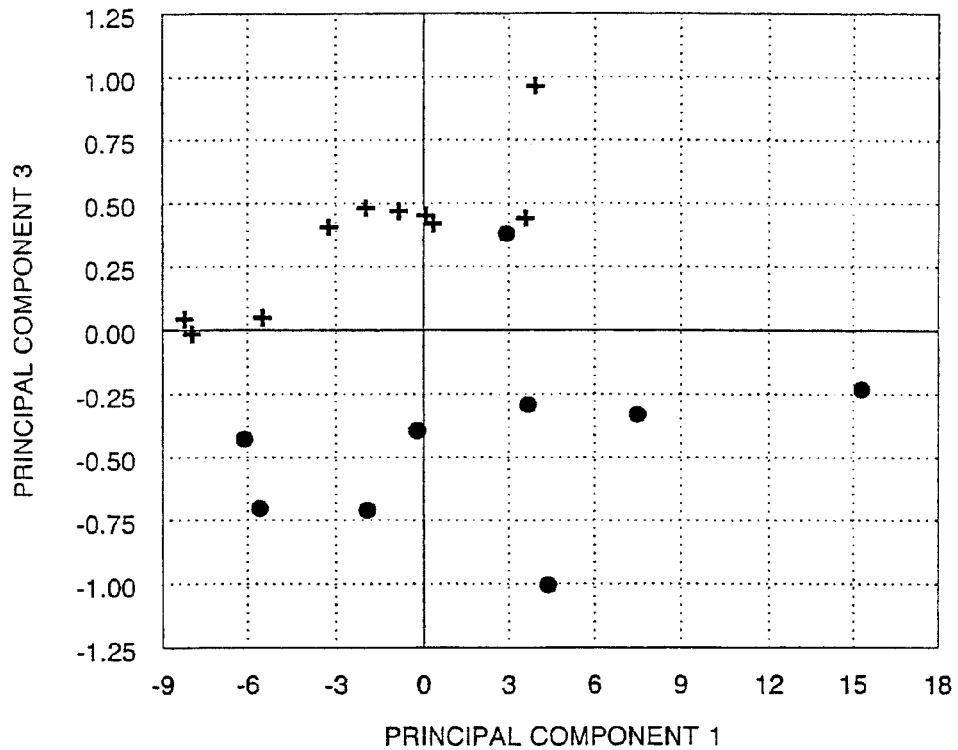
FIG. 4A displays a scoreplot obtained from principal component analysis of spectral data collected from Douglas-fir somatic embryos at the cotyledonary stage (genotype 2) that have "good" and "poor" embryo morphology. The units on the PC axes are universal standard deviations for the set.
Figure 4B:
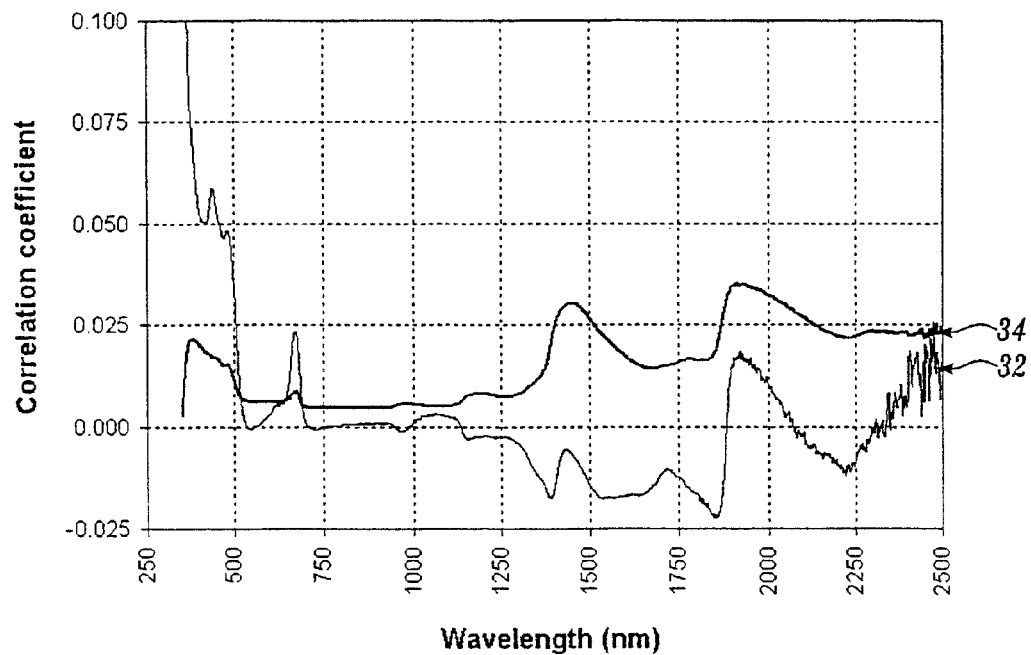
FIG. 4B shows the loadings spectra for each PC depicted in FIG. 4A. Each curve shows the relative contribution that each wavelength makes in accounting for the variance depicted along the scoreplot axes in FIG. B.

A summary of the separation obtained is presented in Table 9. For Douglas-fir, it was possible to draw a straight line on the scoreplot of PC3 versus PC1 that completely separated the high quality ("+") and low quality (black circles) groups (FIG. 4A). Most of this separation occurred along the third PC (FIG. 4B, curve 32), which represented about 2% of the overall variation. PC3 was distinguished in part by absorption bands from pigments in the visible region, including chlorophyll. PC1 (curve 34) represented about 96% of the total spectral variation.

TABLE 9

Cotyledon Stage Somatic Embryos With "High" vs. "Low" Quality Morphology

|  | High Quality Morphology | Low Quality Morphology | PC's Needed | Wavelength/Inferred Chemical Features |
|---|---|---|---|---|
| Douglas-Fir | 10/10* (100%) | 9/9* (100%) | 1 | Water (1450, 1920 nm) |
|  |  |  | 3 | Pigments in visible region shoulder feature (1850-1920 nm) |
| Loblolly Pine | 9/10* (90%) | 9/10* (90%) | 1 | Water (1450, 1920 nm) |
|  |  |  | 3 | Unknown (1400-1500 nm) Lipid (1710, 2300 nm) Bound water (1870 nm) |

*Number correctly classified/number tested

Figure 5A:
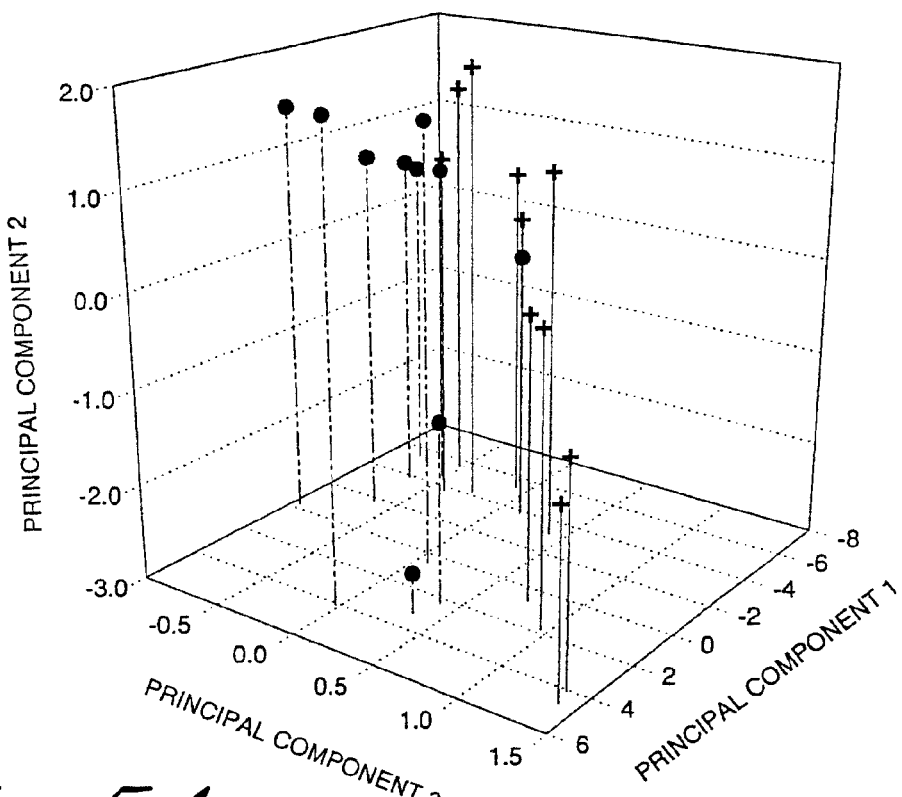
FIG. 5A displays a scoreplot obtained from principal component analysis of spectral data collected from loblolly pine somatic embryos (genotype 5) at the cotyledonary stage that have "good" and "poor" embryo morphology. The units on the PC axes are universal standard deviations for the set.
Figure 5B:
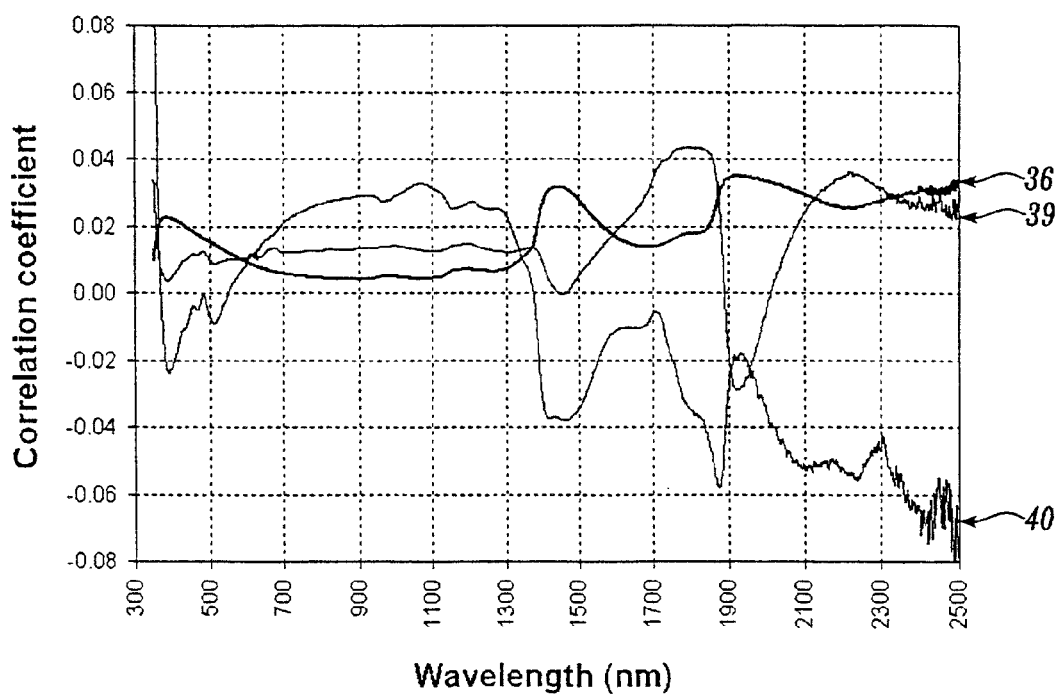
FIG. 5B shows the loadings spectra for each PC depicted in FIG. 5A. Each curve shows the relative contribution that each wavelength makes in accounting for the variance depicted along the scoreplot axes in FIG. 5A.

FIG. 5A shows the scoreplot obtained from loblolly pine somatic embryos having high quality morphology ("+") as compared to embryos having low quality morphology (black circles). Almost complete (90%) separation was achieved, with the first and third PCs combined. In the PC3 loadings spectrum (FIG. 5B, curve 40), there was a strong, slightly bimodal negative peak around 1450 nm (not water), plus putative lipid (1700 and 2300 nm) and bound water (1870 nm) features, as well as absorption peaks in the visible region (380-600 nm). PC3 accounted for about 1% of the total spectral variation. PC1 (curve 36) represented about 95% of the total spectral variation and was mostly water. PCs 1 and 2 combined also provided good separation, the PC2 loadings spectrum (curve 39) being dominated by the shoulder feature between 1760 and 1900 nm. PC2 accounted for about 3% of the total spectral variation. These results demonstrate that principal component analysis of spectral data from somatic embryos having high- and low-quality morphological appearance provides a basis for developing a classification model that will allow somatic embryos to be rapidly categorized with regards to their germination potential.

Principal Component Analysis of Spectra from Somatic Embryos in the Cotyledon (Stage 8) and "Dome" (Stage 5) or "Just Cotyledon" (JC) (Stage 6) Stages Douglas-fir somatic embryos in two distinct developmental stages were selected from plates of genotype 3. Somatic embryos in the cotyledon stage are known to have a much higher frequency of germination than somatic embryos that are in the less mature "dome" or "just cotyledonary" (JC) developmental stages.

Figure 6A:
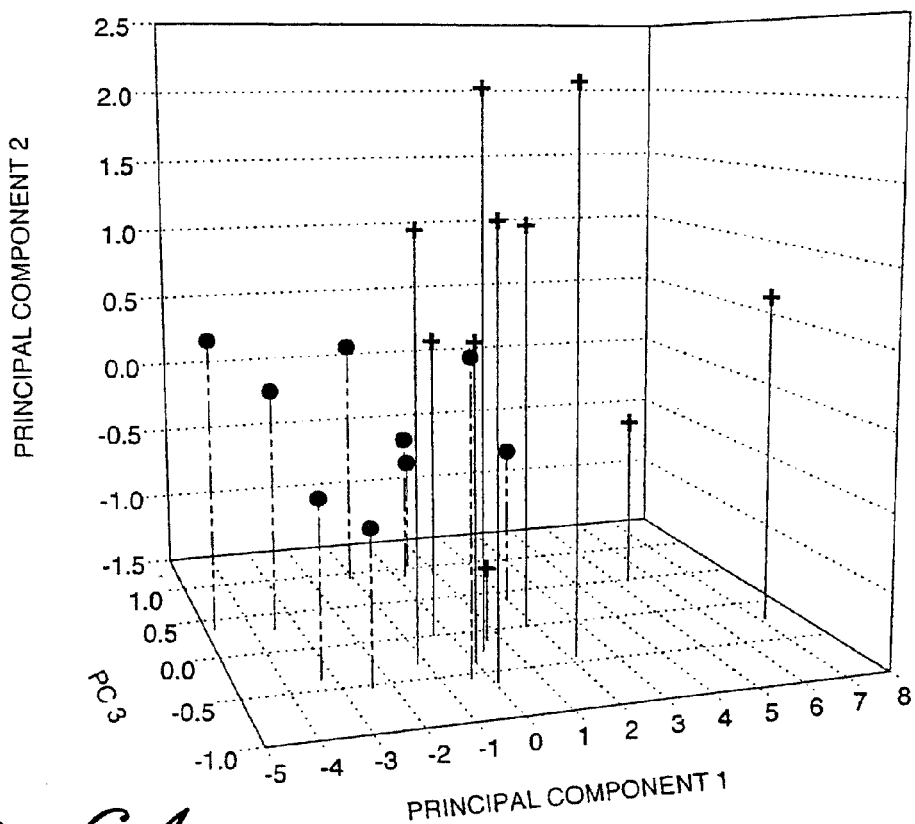
FIG. 6A displays a scoreplot obtained from principal component analysis of spectral data collected from Douglas-fir somatic embryos (genotype 3). The scanned somatic embryos were of two different developmental stages, the cotyledon stage and "dome" or "just cotyledon" stage. The units on the PC axes are universal standard deviations for the set.
Figure 6B:
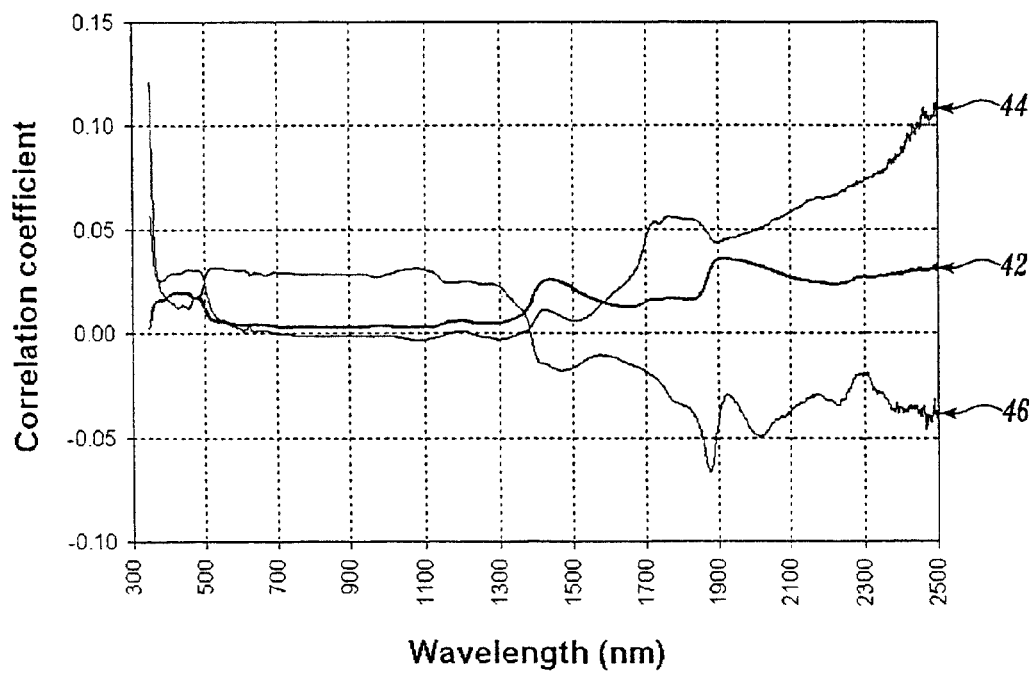
FIG. 6B shows the loadings spectra for each PC depicted in FIG. 6A. Each curve shows the relative contribution that each wavelength makes in accounting for the variance depicted along the scoreplot axes in FIG. 6A.

Dome/JC embryos (black circles in FIG. 6A) and cotyledonary (stage 8) embryos ("+") that were plucked from the same plate formed two distinct groups on a 3D scoreplot formed from PCs 1-3, such that only one embryo of the 19 just fell within the wrong group (FIG. 6A). The strongest contributors to separation were PCs 1 (curve 42) and 2 (curve 44), which are associated with (1) water and (2) lipid, possibly protein N-H, regions, plus the 1800 nm 'shoulder' feature, respectively (FIG. 6B). PCs 1 and 2 account for 82% and 9% of the total spectral variation, respectively, whereas PC 3 (curve 46) accounted for 4% of the total spectral variation. Table 10 presents a summary of the accuracy of the spectral separations obtained using the cotyledon stage and "dome" or "just cotyledonary" stage somatic embryos.

TABLE 10

Cotyledon vs. Earlier Developmental Stages of Douglas-Fir Somatic Embryos From Genotype 3

| Cotyledon Stage | "Dome" or "Just Cotyledon" Stage | PC's Needed | Wavelength/Inferred Chemical Features |
|---|---|---|---|
| 10/10* (100%) | 8/9* (89%) | 1 | Water |
|  |  | 2 | Lipid (1700-1800 nm) Unknown (1420 nm) |

*Number correctly classified/number tested

These results demonstrate that NIR spectral data can accurately distinguish between early developmental stages of somatic embryos, which are germination-incompetent, and the final stage of development on petri plates (approximately equivalent to zygotic stage 8 embryos), many of which are capable of germinating and producing seedlings.

Principal Component Analysis of Spectra From Cold-treated and Control Somatic Embryos Subjecting embryos to a 4-7° C. cold treatment on low-osmolality media in the dark for 1-5 weeks may increase the frequency of subsequent embryo germination by 20 to 200%.

Figure 7A:
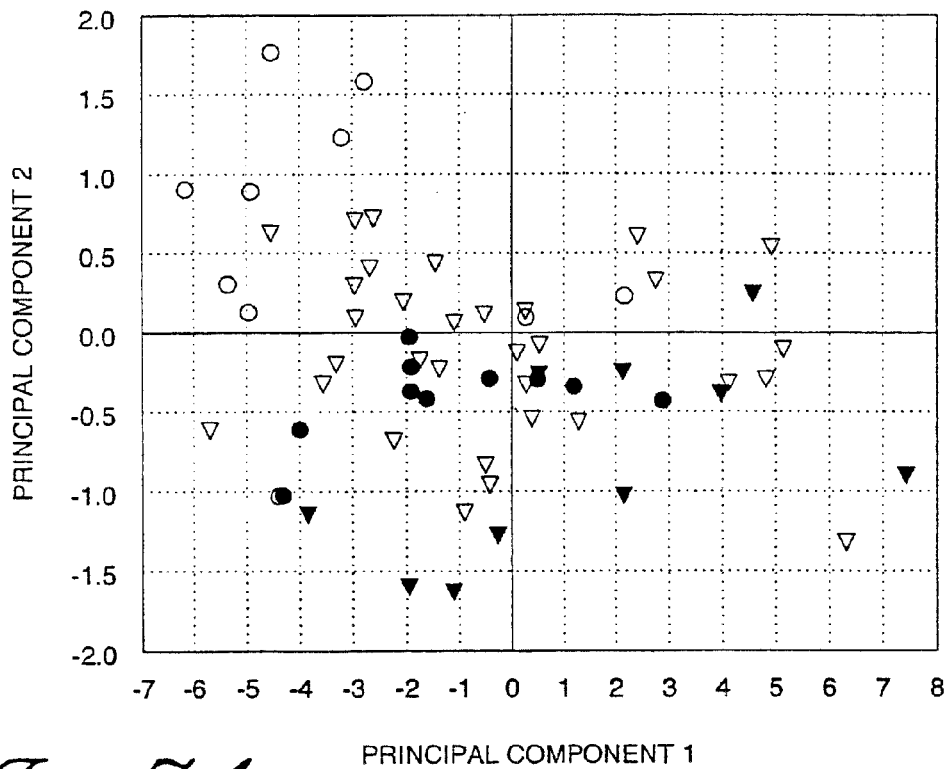
FIG. 7A displays a scoreplot obtained from principal component analysis of spectral data collected from Douglas-fir somatic embryos (genotypes 3 and 4). A set of somatic embryos from each genotype were either subjected to a cold treatment (which improves germination) or received no cold treatment (Control). The units on the PC axes are universal standard deviations for the set.
Figure 7B:
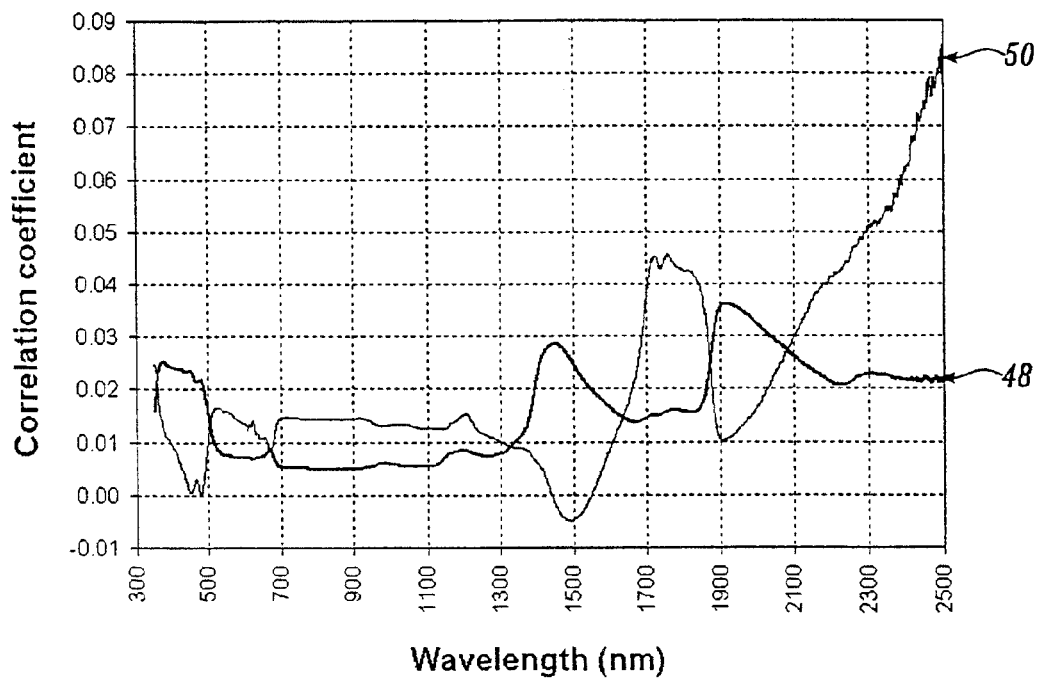
FIG. 7B shows the loadings spectra for each PC depicted in FIG. 7A. Each curve shows the relative contribution that each wavelength makes in accounting for the variance depicted along the scoreplot axes in FIG. 7A.

Principal component analysis of spectral data collected from cold-treated and control Douglas-fir somatic embryos of two genotypes (3 and 4) are presented in FIGS. 7A and 7B. In FIG. 7A solid black circles or triangles identify cold-treated embryos for genotypes 3 and 4, respectively, and the corresponding open symbols identify non-cold-treated embryos of the same two genotypes. For each genotype, a straight line can be drawn that will largely separate the two populations with the degree of success (from 79-100%) shown in Table 11. The separation was determined mainly by the PC2 axis, whose loadings spectrum (FIG. 7B, curve 50) has both lipid and pigment components and accounts for about 4% of the total spectral variation. PC1 (curve 48) accounts for about 91% of the spectral variation.

TABLE 11

Somatic Embryos That Have or Have Not Received Cold Treatment

| Species and Genotype | Control | Cold-treated | PC's Needed | Specific Wavelength/Inferred Chemical Features |
|---|---|---|---|---|
| Douglas-Fir |  |  |  |  |
| Genotype 3 | 9/10* (90%) | 10/10* (100%) | 2 | Lipids (1700-1750 nm) Shoulder region (1800-1900 nm) |
| Genotype 4 | 26/33* (79%) | 9/10* (90%) | 1 | Water |
| Loblolly Pine |  |  |  |  |
| Genotype 5 | 19/20* (95%) | 10/10* (100%) | 1 | Water |
| Genotype 7 | 28/40* (70%) | 17/20* (85%) | 3 | Lipid (1700-1750 nm) |
|  |  |  | 2 | Shoulder region (1800-1900 nm) |

*Number correctly classified/number tested

Figure 8A:
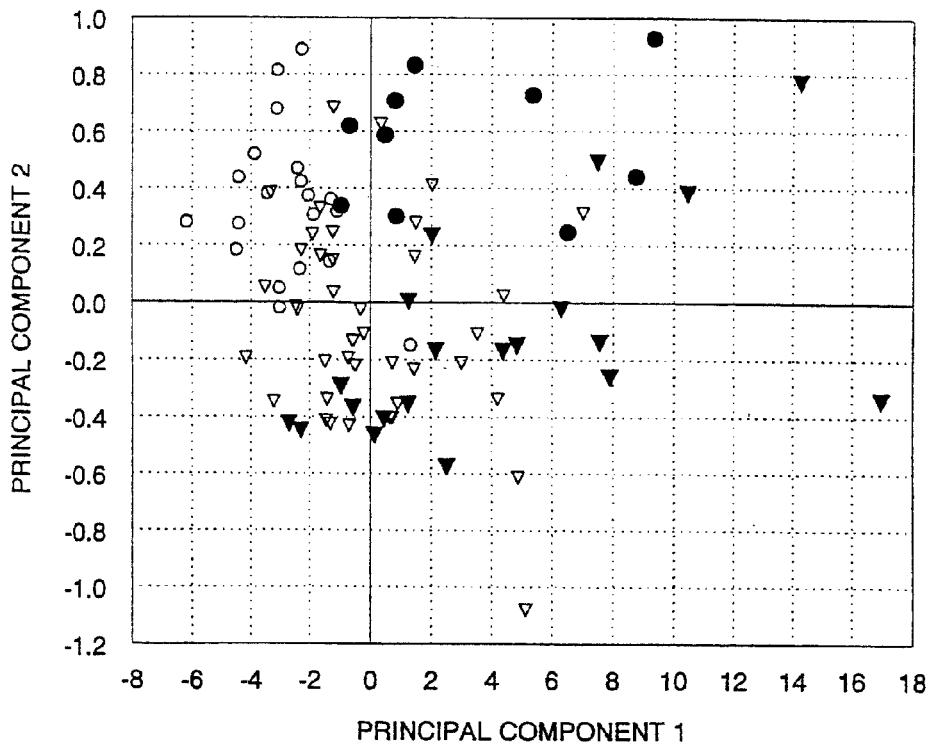
FIG. 8A displays a scoreplot obtained from principal component analysis of spectral data collected from loblolly pine somatic embryos (genotypes 5 and 7) at the cotyledonary stage. A set of somatic embryos from each genotype were either subjected to a cold treatment (which improves germination) or received no cold treatment (Control). The units on the PC axes are universal standard deviations for the set.
Figure 8B:
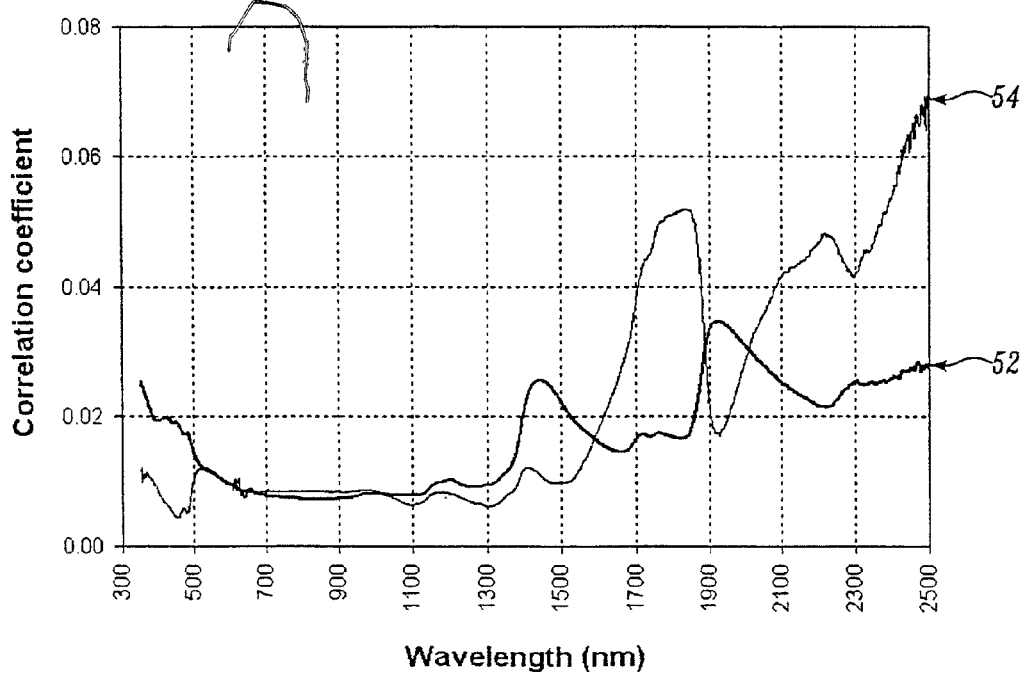
FIG. 8B shows the loadings spectra for each PC depicted in FIG. 8A. Each curve shows the relative contribution that each wavelength makes in accounting for the variance depicted along the scoreplot axes in FIG. 8A.

The results of principal component analysis for the equivalent contrast using loblolly pine somatic embryos appears in FIGS. 8A and 8B. Loblolly pine somatic embryos from genotype 5 (circles) exhibit a clear separation of cold-treated (solid circles) and control groups (open circles) in (FIG. 8A). Loblolly pine genotype 7 (triangles) exhibits a similar tendency in regard to these two treatment groups. In general, embryos that were partially dried then cold-treated show higher, and greater variation in, water contents than those that were not. The separations, for each genotype, were by PCs 1 and 2 combined, which incorporate the water, lipid and 1800-1900 nm shoulder features noted for Douglas-fir. PC1 (curve 52) and PC2 (curve 54) account for 92% and 4% of the total spectral variation, respectively.

These results demonstrate that NIR spectral data can distinguish between developmentally similar (approx. stage 8) somatic embryos having higher germination potential (on account of prior cold or cold and partial drying treatment) from those embryos of lower germination potential (having not received such treatments).

While the preferred embodiment of the invention has been illustrated and described, it will be appreciated that various changes can be made therein without departing from the spirit and scope of the invention.

The invention claimed is:

1. A method for classifying plant embryos according to their germination potential, comprising:
   (a) developing a classification model by
      (i) acquiring raw digital image data of reference samples of whole plant embryos or of embryo organs of known germination potential;
      (ii) performing a data analysis by applying one or more classification algorithms to the acquired raw digital image data, wherein at least one of the one or more classification algorithms uses non-perimeter information, the non-perimeter information being more than an embryo perimeter from the acquired raw digital image data, the data analysis resulting in development of a classification model for classifying plant embryos by their germination potential;
   (b) acquiring raw digital image data of a plant embryo or a plant embryo organ of unknown germination potential; and
   (c) applying the developed classification model to the raw digital image data of step (b) in order to classify the plant embryo of unknown germination potential according to its presumed germination potential.

2. The method according to claim 1 wherein the raw digital image data acquired in step (a)(i) is preprocessed using one or more preprocessing algorithms before step (a)(ii); the raw digital image data acquired in step (b) is preprocessed using one or more preprocessing algorithms; and step (c) is carried out using the preprocessed raw digital image data.

3. The method according to claim 2 wherein the preprocessing algorithm removes raw image data that is not from the plant embryo or plant embryo organ.

4. The method according to claim 2 wherein the preprocessing algorithm reduces the amount of raw image data yet retains substantially all of the embryo or embryo organ geometric information.

5. The method according to claim 2 wherein the preprocessing algorithm calculates metrics.

6. The method according to claim 1 wherein the raw digital image data is acquired from more than one view of the plant embryo or plant embryo organ.

7. The method according to claim 1 wherein the plant embryo is a plant somatic embryo.

8. The method according to claim 1 wherein the plant is a tree.

9. The method according to claim 8 wherein the tree is a member of the order Coniferales.

10. The method according to claim 8 wherein the tree is a member of the family Pinaceae.

11. The method according to claim 8 wherein the tree is selected from the group consisting of genera *Pseudotsuga* and *Pinus*.

12. The method according to claim 1 wherein the non-perimeter information comprises a skewness coefficient.

13. The method according to claim 1 wherein the non-perimeter information comprises a kurtosis coefficient.

14. The method according to claim 1 wherein the non-perimeter information comprises a mean value of a detail coefficient.

15. The method according to claim 1 wherein the at least one of the one or more classification algorithms using non-perimeter information also uses perimeter information.

16. The method according to claim 15 wherein the perimeter information comprises perimeter radii from a top view of the reference samples.

17. The method according to claim 1 wherein the classification model is a single metric classification model and the step of performing a data analysis by applying one or more classification algorithms to the acquired raw digital image data further comprises:
   (i) calculating a metric value from the acquired raw digital image data of each embryo of known germination potential;
   (ii) dividing the metric values obtained in step (i) into two sets of metric values according to their known germination potential;
   (iii) calculating a Lorenz curve from the two sets of metric values;
   (iv) using any point on the Lorenz curve calculated in step (iii) as a threshold value to arrive at a single metric classification model for classifying plant embryos by their germination potential.

18. The method according to claim 1 wherein the raw digital image data comprises at least one of: absorption spectral raw data, transmittance spectral raw data, and reflectance spectral raw data.

* * * * *